(12) United States Patent
Paranhos-Baccala et al.

(10) Patent No.: US 7,771,927 B1
(45) Date of Patent: Aug. 10, 2010

(54) MULTIPLE SCLEROSIS-ASSOCIATED RETROVIRAL (MSRV) NUCLEIC ACIDS CORRESPONDING TO THE ENV REGION

(75) Inventors: Glaucia Paranhos-Baccala, Lyons (FR); Florence Komurian-Pradel, Poleymieux Au Mont d'Or (FR); Frederic Bedin, Lyons (FR); Mireille Sodoyer, Sainte Foy les Lyon (FR); Catherine Ott, Lyons (FR); Francois Mallet, Villeurbanne (FR); Herve Perron, Lyons (FR); Bernard Mandrand, Villeurbanne (FR)

(73) Assignee: Biomerieux, Marcy l'Etoile (FR)

( * ) Notice: Subject to any disclaimer, the term of this patent is extended or adjusted under 35 U.S.C. 154(b) by 0 days.

(21) Appl. No.: 09/319,156

(22) PCT Filed: Jul. 7, 1998

(86) PCT No.: PCT/FR98/01460

§ 371 (c)(1),
(2), (4) Date: Nov. 2, 1999

(87) PCT Pub. No.: WO98/02666

PCT Pub. Date: Jan. 21, 1999

(30) Foreign Application Priority Data

Jul. 7, 1997 (FR) .................................. 97 08816

(51) Int. Cl.
C12Q 1/70 (2006.01)
C07H 21/04 (2006.01)
A61K 39/21 (2006.01)

(52) U.S. Cl. ...................... 435/5; 536/23.72; 424/207.1
(58) Field of Classification Search .............. 424/186.1, 424/204.1, 187.1, 207.1; 536/29.72, 23.72
See application file for complete search history.

(56) References Cited

U.S. PATENT DOCUMENTS 6,582,703 B2 * 6/2003 Perron et al. .............. 424/204.1

FOREIGN PATENT DOCUMENTS

| FR | 2 689 519 | 10/1993 |
|---|---|---|
| FR | 2 689 520 | 10/1993 |
| FR | 2 689 521 | 10/1993 |
| FR | 2 715 936 | 8/1995 |
| FR | 2 715 937 | 8/1995 |
| FR | 2 715 938 | 8/1995 |
| FR | 2 715 939 | 8/1995 |
| FR | 2 716 198 | 8/1995 |
| FR | 2 727 428 | 5/1996 |
| FR | 2 728 585 | 6/1996 |
| FR | 2 731 356 | 9/1996 |
| FR | 2 737 500 | 2/1997 |
| WO | WO 93/07259 | 4/1993 |
| WO | WO 93/20188 | 10/1993 |
| WO | WO 94/28138 | 12/1994 |
| WO | WO 95/21256 | 8/1995 |
| WO | WO 97/06260 | 2/1997 |
| WO | WO 98/23755 | 6/1998 |

OTHER PUBLICATIONS

Boehringer Mannheim Biochemicals, 1994 Catalog, "Random Primed DNA Labeling Kit", p. 103.*
Pauley, A., "The Sequence of H. Sapiens BAC Clone RG083M05," unpublished paper, 1996, pp. 1-20.
Boysen, C. et al., "Analysis of the 1.1-Mb Human Alpha/Delta T-Cell Receptor Locus with Bacterial Artificial Chromosome Clones," Molecular Biotechnology, University of Washington Database, 1997, pp. 1-4.
Adams, M.D. et al., "Initial Assessment of Human Gene Diversity and Expression Patterns Based Upon 83 Million Nucleotides of cDNA Sequence," The Institute for Genomic Research, 1995, pp. 1-4.
La Mantia, Girolama et al., "Identification and Characterization of Novel Human Endogenous Retroviral Sequences Prefenrtially Expressed in Undifferentiated Embryonal Carcinoma Cells," Nucleic Acids Research, vol. 19, No. 7, pp. 1513-1520.
Perron, H. et al., "Molecular Identification of a Novel Retrovirus Repeatedly Isolated from Patients with Multiple Sclerosis," Proc. Natl. Acad. Sci. USA, vol. 94, pp. 7583-7588.
Laemmli, U. K., "Cleavage of Structural Proteins during the Assembly of the Head of Bacteriophage T4," Nature, vol. 227, pp. 680-685, Aug. 15, 1970.
Towbin, Harry et al., "Electrophoretic transfer of proteins from polyacrylamide gels to nitrocellulose sheets: Procedure and some applications," Proc. Natl. Acad. Sci. USA, vol. 76, No. 9, pp. 4350-4354, Sep. 1979.

* cited by examiner

Primary Examiner—Jeffrey S. Parkin
(74) Attorney, Agent, or Firm—Oliff & Berridge, PLC

(57) ABSTRACT

The invention concerns a nucleic material, in isolated or purified state, and a nucleotide fragment comprising a nucleotide sequence selected from the group consisting in (i) the sequences SEQ ID NO: 112, SEQ ID NO:114, SEQ ID NO: 117, SEQ ID NO: 120, SEQ ID NO. 124, SEQ ID NO: 130, SEQ ID NO: 141 and SEQ ID NO: 142, (ii) the complementary sequences of sequences (i); and (iii) the sequences equivalent to sequences (ii) and (iii), in particular the sequence having for every series of 100 contiguous monomers, at least 50%, preferably 70% homology with sequences (i) and (ii) respectively. The invention also concerns their uses for detecting a retrovirus associated with multiple sclerosis and/or rheumatoid arthritis.

13 Claims, 33 Drawing Sheets

Fig. 2

```
          10         20         30         40         50
  1234567890 1234567890 1234567890 1234567890 1234567890
  GCTTATAGAA GGACCCCTAG TATGGGGTAA TCCCCTCTGG GAAACCAAGC        50
  A  Y  R  R    T  P  S     M  G  .     S  P  L  G     N  Q  A
    L  I  E    G  P  L  V    W  G  .    P  L  W  E    T  K  P
      L  .  K    D  P  .    Y  G  V    I  P  S  G    K  P  S

CCCAGTACTC AGCAGGAAAA ATAGAATAGG AAACCTCACA AGGACATACT       100
   P  V  L    S  R  K  N    R  I  G    N  L  T    R  T  Y  F
    Q  Y  S    A  G  K    I  E  .  E    T  S  Q    G  H  T
  P  S  T    Q  Q  E  K    .  N  R    K  P  H    K  D  I  L

TTCCTCCCCT CCAGATGGCT AGCCACTGAG GAAGGAAAAA TACTTTCACC       150
    P  P  L    Q  M  A    S  H  .  G    R  K  N    T  F  T
  F  L  P  S    R  W  L    A  T  E    E  G  K  I    L  S  P
    S  S  P    P  D  G  .    P  L  R    K  E  K    Y  F  H  L

TGCAGCTAAC CAACAGAAAT TACTTAAAAC CCTTCACCAA ACCTTCCACT       200
   C  S  .    P  T  E  I    T  .  N    P  S  P  N    L  P  L
    A  A  N    Q  Q  K  L    L  K  T    L  H  Q    T  F  H  L
      Q  L  T    N  R  N    Y  L  K  P    F  T  K    P  S  T

TAGGCATTGA TAGCACCCAT CAGATGGCCA AATTATTATT TACTGGACCA       250
   R  H  .  .    H  P  S    D  G  Q    I  I  I    Y  W  T  R
    G  I  D    S  T  H    Q  M  A  K    L  L  F    T  G  P
      .  A  L  I    A  P  I    R  W  P    N  Y  Y  L    L  D  Q

GGCCTTTTCA AAACTATCAA GAAGATAGTC AGGGGCTGTG AAGTGTGCCA       300
    P  F  Q    N  Y  Q    E  D  S  Q    G  L  .    S  V  P
  G  L  F  K    T  I  K    K  I  V    R  G  C  E    V  C  Q
   A  F  S    K  L  S  R  R    .  S    G  A  V    K  C  A  K

AAGAAATAAT                                                   310
  K  K  .
    R  N  N
      E  I
```

```
CCCTGTATCT TTAACCTCCT TGTTAAGTTT GTCTCTTCCA GAATCAAAAC        50
 P C I F    N L L      V K F      V S S R I    K T
  P V S     L T S L    L S L      S L P E S    K L
   L Y L    . P P     C . V C     L F Q       N Q N

TGTAAAACTA CAAATTGTTC TTCAAATGGA GCACCAGATG GAGTCCATGA       100
 V K L     Q I V L    Q M E      H Q M E     S M T
  . N Y    K L F      F K W S    T R W       S P .
   C K T T  N C S     S N G      A P D G     V H D

CTAAGATCCA CCGTGGACCC CTGGACCGGC CTGCTAGCCC ATGCTCCGAT       150
  K I H    R G P      L D R P    A S P      C S D
  L R S T  V D P      W T G      L L A H    A P M
   . D P    P W T P   G P A     C . P       M L R C

GTTAATGACA TTGAAGGCAC CCCTCCCGAG GAAATCTCAA CTGCACAACC       200
 V N D I   E G T      P P E      E I S T   A Q P
  L M T    L K A P    L P R      K S Q     L H N P
   . . H   . R H      P S R G    N L N     C T T

CCTACTATGC CCCAATTCAG CGGGAAGCAG TTAGAGCGGT CATCAGCCAA       250
 L L C     P N S A    G S S      . S G    H Q P T
  Y Y A    P I Q      R E A V    R A V    I S Q
   P T M P  Q F S     G K Q      L E R S   S A N

CCTCCCCAAC AGCACTTGGG TTTTCCTGTT GAGAGGGGGG ACTGAGAGAC       300
 S P T     A L G      F S C      . E G G  L R D
  P P Q Q  H L G      F P V      E R G D  . E T
   L P N   S T W V    F L L      R G G    T E R Q

AGGACTAGCT GGATTTCCTA GGCCAACGAA GAATCCCTAA GCCTAGCTGG       350
 R T S W   I S .      A N E      E S L S  L A G
  G L A    G F P R    P T K      N P .    A . L G
   D . L   D F L      G Q R R    I P K    P S W
```

| | |
|---|---|
| GAAGGTGACT GCATCCACCT CTAAACATGG GGCTTGCAAC TTAGCTCACA<br> K  V  T    A S T S    K H G    A C N    L A H T<br> R  .  L    H P P    L N M G    L A T    . L T<br>E  G  D  C    I H L    . T W    G L Q    L  S S H | 400 |
| CCCGACCAAT CAGAGAGCTC ACTAAAATGC TAATTAGGCA AAAATAGGAG<br>  R P I    R E L    T K M L    I R Q    K  .  E<br>P  D Q  S    E S S    L K C    . L G K    N R R<br>  P T N    Q R A H    . N A N    . A    K I G G | 450 |
| GTAAAGAAAT AGCCAATCAT CTATTGCCTG AGAGCACAGC GGGAGGGACA<br>V  K  K    .  P I I    Y C L    R A Q R    E G Q<br> .  R N    S Q S S    I A    . E H S    G R D K<br>  K E I    A N H    L L P E    S T A    G G T | 500 |
| AGGATCGGGA TATAAACCCA GGCATTCGAG CCGGCAACGG CAACCCCCTT<br> G  S  G    Y K P    R H S    S R Q R    Q P P L<br>D  R  D    I N P    G I R    A G N G    N P L<br> R  I  G  I    . T Q    A F E    P A T A    T P F | 550 |
| TGGGTCCCCT CCCTTTGTAT GGGCGCTCTG TTTTCACTCT ATTTCACTCT<br>  G P L    P L Y    G R S V    F T L    F H S<br>W  V  P  S    L C M    G A L    F S L Y    F T L<br> G  S P    P F V W    A L C    F H S    I S L Y | 600 |
| ATTAAATCTT GCAACTGAAA AAAAAAAAA AAAAA<br>I  K  S  C    N  .  K    K K K    K<br> L  N  L    A T E K    K K K    K<br>  . I L    Q L K    K K K K    K | 635 |

Fig. 4A

```
           10         20         30         40         50
     1234567890 1234567890 1234567890 1234567890 1234567890
     ATGGCCCTCC CTTATCATAC TTTTCTCTTT ACTGTTCTCT TACCCCCTTT       50
      M  A  L  P   Y  H  T   F  L  F   T  V  L  L   P  P  F
       W  P  S   L  I  I  L   F  S  L   L  F  S   Y  P  L  S
        G  P  P   L  S  Y   F  S  L  Y   C  S  L   T  P  F

CGCTCTCACT GCACCCCCTC CATGCTGCTG TACAACCAGT AGCTCCCCTT      100
      A  L  T   A  P  P  P   C  C  C   T  T  S   S  S  P  Y
       L  S  L   H  P  L   H  A  A  V   Q  P  V   A  P  L
        R  S  H  C   T  P  S   M  L  L   Y  N  Q  .   L  P  L

ACCAAGAGTT TCTATGAAGA ACGCGGCTTC CTGGAAATAT TGATGCCCCA      150
      Q  E  F   L  .  R   T  R  L  P   G  N  I   D  A  P
       T  K  S  F   Y  E  E   R  G  F   L  E  I  L   M  P  H
        P  R  V   S  M  K  N   A  A  S   W  K  Y  .   C  P  I

TCATATAGGA GTTTATCTAA GGGAAACTCC ACCTTCACTG CCCACACCCA      200
      S  Y  R  S   L  S  K   G  N  S   T  F  T  A   H  T  H
       H  I  G   V  Y  L  R   E  T  P   P  S  L   P  T  P  I
        I  .  E   F  I  .   G  K  L  H   L  H  C   P  H  P

TATGCCCCGC AACTGCTATA ACTCTGCCAC TCTTTGCATG CATGCAAATA      250
      M  P  R   N  C  Y  N   S  A  T   L  C  M   H  A  N  T
       C  P  A   T  A  I   T  L  P  L   F  A  C   M  Q  I
        Y  A  P  Q   L  L  .   L  C  H   S  L  H  A   C  K  Y

CTCATTATTG GACAGGGAAA ATGATTAATC CTAGTTGTCC TGGAGGACTT      300
       H  Y  W   T  G  K   M  I  N  P   S  C  P   G  G  L
       L  I  I  G   Q  G  K   .  L  I   L  V  V  L   E  D  L
        S  L  L   D  R  E  N   D  .  S   .  L  S   W  R  T  W

GGAGCCACTG TCTGTTGGAC TTACTTCACC CATACCAGTA TGTCTGATGG      350
      G  A  T  V   C  W  T   Y  F  T   H  T  S  M   S  D  G
       E  P  L   S  V  G  L   T  S  P   I  P  V   C  L  M  G
        S  H  C   L  L  D   L  L  H  P   Y  Q  Y   V  .  W
```

Fig. 4B

```
            10          20          30          40          50
     1234567890  1234567890  1234567890  1234567890  1234567890
     GGGTGGAATT  CAAGGTCAGG  CAAGAGAAAA  ACAAGTAAAG  GAAGCAATCT      400
       G  G  I    Q  G  Q    R  E  K     Q  V  K     E  A  I  S
        V  E  F    K  V  R    Q  E  K  N    K  *  R    K  Q  S
     G  W  N  S    R  S  G    K  R  K     T  S  K  G    S  N  L

CCCAACTGAC  CCGGGGACAT  AGCACCCCTA  GCCCCTACAA  AGGACTAGTT      450
       Q  L  T    R  G  H     S  T  P  S    P  Y  K    G  L  V
      P  N  *  P    G  D  I    A  P  L    A  P  T  K    D  *  F
     P  T  D     P  G  T  *    H  P  *    P  L  Q      R  T  S  S

CTCTCAAAAC  TACATGAAAC  CCTCCGTACC  CATACTCGCC  TGGTGAGCCT      500
       L  S  K  L   H  E  T    L  R  T     H  T  R  L    V  S  L
        S  Q  N    Y  M  K  P   S  V  P    I  L  A    W  *  A  Y
     L  K  T       T  *  N    P  P  Y  P    Y  S  P     G  E  P

ATTTAATACC  ACCCTCACTC  GGCTCCATGA  GGTCTCAGCC  CAAAACCCTA      550
       F  N  T     T  L  T  R   L  H  E     V  S  A    Q  N  P  T
        L  I  P    P  S  L     G  S  M  R   S  Q  P     K  T  L
     I  *  Y  H    P  H  S    A  P  *      G  L  S  P    K  P  Y

CTAACTGTTG  GATGTGCCTC  CCCCTGCACT  TCAGGCCATA  CATTTCAATC      600
       N  C  W    M  C  L     P  L  H  F    R  P  Y    I  S  I
      L  T  V  G    C  A  S    P  C  T     S  G  H  T    F  Q  S
      *  L  L     D  V  P  P    P  A  L    Q  A  I      H  F  N  P

CCTGTTCCTG  AACAATGGAA  CAACTTCAGC  ACAGAAATAA  ACACCACTTC      650
       P  V  P  E   Q  W  N    N  F  S     T  E  I  N    T  T  S
       L  F  L    N  N  G  T    T  S  A    Q  K  *     T  P  L  P
       C  S  *    T  M  E      Q  L  Q  H    R  N  K    H  H  F

CGTTTTAGTA  GGACCTCTTG  TTTCCAATCT  GGAAATAACC  CATACCTCAA      700
       V  L  V    G  P  L     V  S  N  L    E  I  T    H  T  S  N
        F  *  *   D  L  L      F  P  I  W   K  *  P     I  P  Q
     R  F  S  R    T  S  C    F  Q  S      G  N  N  P    Y  L  K
```

Fig. 4C

```
          10         20         30         40         50
 1234567890 1234567890 1234567890 1234567890 1234567890
 ACCTCACCTG TGTAAAATTT AGCAATACTA TAGACACAAC CAGCTCCCAA    750
   L  T  C  V  K  F  S  N  T  I  D  T  T  S  S  Q
  T  S  P  V  .  N  L  A  I  L  .  T  Q  P  A  P  N
 P  H  L  C  K  I  .  Q  Y  Y  R  H  N  Q  L  P  M

TGCATCAGGT GGGTAACACC TCCCACACGA ATAGTCTGCC TACCCTCAGG    800
   C  I  R  W  V  T  P  P  T  R  I  V  C  L  P  S  G
  A  S  G  G  .  H  L  P  H  E  .  S  A  Y  P  Q  E
 H  Q  V  G  N  T  S  H  T  N  S  L  P  T  L  R

AATATTTTTT GTCTGTGGTA CCTCAGCCTA TCATTGTTTG AATGGCTCTT    850
   I  F  F  V  C  G  T  S  A  Y  H  C  L  N  G  S  S
  Y  F  L  S  V  V  P  Q  P  I  I  V  .  M  A  L
 N  I  F  C  L  W  Y  L  S  L  S  L  F  E  W  L  F

CAGAATCTAT GTGCTTCCTC TCATTCTTAG TGCCCCCTAT GACCATCTAC    900
   E  S  M  C  F  L  S  F  L  V  P  P  M  T  I  Y
  Q  N  L  C  A  S  S  H  S  .  C  P  L  .  P  S  T
 R  I  Y  V  L  P  L  I  L  S  A  P  Y  D  H  L  H

ACTGAACAAG ATTTATACAA TCATGTCGTA CCTAAGCCCC ACAACAAAAG    950
   T  E  Q  D  L  Y  N  H  V  V  P  K  P  H  N  K  R
  L  N  K  I  Y  T  I  M  S  Y  L  S  P  T  T  K  E
 .  T  R  F  I  Q  S  C  R  T  .  A  P  Q  Q  K

AGTACCCATT CTTCCTTTTG TTATCAGAGC AGGAGTGCTA GGCAGACTAG   1000
   V  P  I  L  P  F  V  I  R  A  G  V  L  G  R  L  G
  Y  P  F  F  L  L  L  S  E  Q  E  C  .  A  D  .
 S  T  H  S  S  F  C  Y  Q  S  R  S  A  R  Q  T  R

GTACTGGCAT TGGCAGTATC ACAACCTCTA CTCAGTTCTA CTACAAACTA   1050
   T  G  I  G  S  I  T  T  S  T  Q  F  Y  Y  K  L
  V  L  A  L  A  V  S  Q  P  L  L  S  S  T  T  N  Y
 Y  W  H  W  Q  Y  H  N  L  Y  S  V  L  L  Q  T  I
```

Fig. 4D

```
          10         20         30         40         50
 1234567890 1234567890 1234567890 1234567890 1234567890
TCTCAAGAAA TAAATGGTGA CATGGAACAG GTCACTGACT CCCTGGTCAC   1100
  S Q E I   N G D  M E Q    V T D S    L V T
  L K K   . M V T   W N R    S L T    P W S P
  S R N     K W .   H G T  G H . L     P G H

CTTGCAAGAT CAACTTAACT CCCTAGCAGC AGTAGTCCTT CAAAATCGAA   1150
  L Q D     Q L N S   L A A    V V L    Q N R R
  C K I     N L T P   . Q Q    . S F    K I E
  L A R S   T . L     P S S  S S P S    K S K

GAGCTTTAGA CTTGCTAACC GCCAAAAGAG GGGGAACCTG TTTATTTTTA   1200
  A L D     L L T A   K R G    G T C    L F L
  E L . T   . C . P   P K E    G E P    V Y F .
  S F R     L A N R   Q K R    G N L    F I F R

GGAGAAGAAC GCTGTTATTA TGTTAATCAA TCCAGAATTG TCACTGAGAA   1250
  G E E R   C Y Y    V N Q    S R I V    T E K
  E K N     A V I M  L I N    P E L      S L R K
  R R T     L L L C  . S I    Q N C     H . E

AGTTAAAGAA ATTCGAGATC GAATACAATG TAGAGCAGAG GAGCTTCAAA   1300
  V K E     I R D R   I Q C    R A E     E L Q N
  L K K     F E I     E Y N V  E Q R     S F K
  S . R N   S R S     N T M    . S R    G A S K

ACACCGAACG CTGGGGCCTC CTCAGCCAAT GGATGCCCTG GGTTCTCCCC   1350
  T E R     W G L     L S Q W  M P W    V L P
  T P N A   G A S     S A N    G C P    G F S P
  H R T     L G P P   Q P M    D A L    G S P L

TTCTTAGGAC CTCTAGCAGC TCTAATATTG TTACTCCTCT TTGGACCCTG   1400
  F L G P   L A A     L I L    L L F    G P C
  S . D L   . Q L     . Y C    Y S S    L D P V
  L R T     S S S     S N I V  T P L    W T L
```

Fig. 4E

```
          10         20         30         40         50
 1234567890 1234567890 1234567890 1234567890 1234567890
 TATCTTTAAC CTCCTTGTTA AGTTTGTCTC TTCCAGAATT GAAGCTGTAA    1450
  I  F  N   L  L  V  K  F  V  S   S  R  I    E  A  V  K
   S  L  T   S  L  L   S  L  S  L  P  E  L   K  L  .
  Y  L  .  P   P  C  .  V  C  L   F  Q  N  .  S  C  K

AGCTACAGAT GGTCTTACAA ATGGAACCCC A                       1481
  L  Q  M   V  L  Q    M  E  P
   S  Y  R  W  S  Y  K   W  N  P
  A  T  D   G  L  T  N   G  T  P
```

```
TCAAAATCGA AGAGCTTTAG ACTTGCTAAC CGCCAAAAGA GGGGGAACCT    50
 S K S  K S F R  L A N  R Q K R  G N L
  Q N R  R A L D  L L T  A K R  G G T C
   K I E  E L .  T C .  P  P K E  G E P

GTTTATTTTT AGGGGAAGAA TGCTGTTAGT ATGTTAATCA ATCTGGAATC   100
 F I F  R G R M  L L V  . S  I W N H
  L F L  G E E  C C .  Y V N Q  S G I
   V Y F  .  G K N  A V S  M L I N  L E S

ATTACTGAGA AAGTTAAAGA AATTTGAGAT CGAATATAAT GTAGAGCAGA   150
 Y . E  S . R  N L R S  N I M  . S R
  I T E K  V K E  I . D  R I .  C R A E
   L L R  K L K K  F E I  E Y N  V E Q R

GGACCTTCAA AACACTGCAC CCTGGGGCCT CCTCAGCCAA TGGATGCCCT   200
 G P S  K H C T  L G P  P Q P M  D A L
  D L Q  N T A P  W G L  L S Q  W M P W
   T F K  T L H  P G A S  S A N  G C P

GGACTCTCCC CTTCTTAGGA CCTCTAGCAG CTATAATATT TTTACTCCTC   250
 D S P  L L R T  S S S  Y N I  F T P L
  T L P  F L G  P L A A  I I F  L L L
   G L S P  S . D  L . Q  L . Y F  Y S S

TTTGGACCCT GTATCTTCAA CTTCCTTGTT AAGTTTGTCT CTTCCAGAAT   300
 W T L  Y L Q  L P C  . V C L  F Q N
  F G P C  I F N  F L V  K F V S  S R I
   L D P  V S S T  S L L  S L S  L P E L

TGAAGCTGTA AAGCTACAAA TAGTTCTTCA AATGGAACCC CAGATGCAGT   350
 . S C K  A T N  S S S  N G T P  D A V
  E A V  K L Q I  V L Q  M E P  Q M Q S
   K L .  S Y K  . F F K  W N P  R C S
```

Fig. 5B

```
            10         20         30         40         50
    1234567890 1234567890 1234567890 1234567890 1234567890
    CCATGACTAA AATCTACCGT GGACCCCTGG ACCGGCCTGC TAGACTATGC      400
     H  D  .   N  L  P    W  T  P    G  P  A  C     .  T  M  L
      M  T  K   I  Y  R    G  P  L    D  R  P  A   R  L  C
    P  .  L    K  S  T  V   D  P  W   T  G  L  L    D  Y  A

TCTGATGTTA ATGACATTGA AGTCACCCCT CCCGAGGAAA TCTCAACTGC      450
     .  C  .    H  .  S    H  P  S    R  G  N     L  N  C
      S  D  V   N  D  I  E  V  T  P   P  E  E  I   S  T  A
    L  M  L    M  T  L  K   S  P  L   P  R  K      S  Q  L  H

ACAACCCCTA CTACACTCCA ATTCAGTAGG AAGCAGTTAG AGCAGTTGTC      500
     T  T  P  T  T  L  Q   F  S  R    K  Q  L  E   Q  L  S
      Q  P  L   L  H  S  N  S  V  G   S  S  .      S  S  C  Q
    N  P  Y    Y  T  P  I  Q  .  E    A  V  R      A  V  V

AGCCAACCTC CCCAACAGTA CTTGGGTTTT CCTGTTGAGA GGGTGGACTG      550
     A  N  L   P  N  S  T   W  V  F    L  L  R    G  W  T  E
      P  T  S   P  T  V    L  G  F  S   .  E     G  G  L
    S  Q  P  P  Q  Q  Y    L  G  F    P  V  E  R   V  D  .

AGAGACAGGA CTAGCTGGAT TTCCTAGGCT GACTAAGAAT CCCNAAGCCT      600
     R  Q  D   .  L  D     F  L  G   .  L  R  I    P  K  P
    R  D  R  T  S  W  I    S  .  A   D  .  E  S    X  S  L
      E  T  G   L  A  G  F   P  R  L   T  K  N    P  X  A  X

ANCTGGAAG GTGACCGCAT CCATCTTTAA ACATGGGCT TGCAACTTAG        650
     X  W  E  G  D  R  I    H  L  .   T  W  G  L   Q  L  S
      X  G  K   V  T  A  S   I  F  K   H  G  A    C  N  L  A
    L  G  R    .  P  H    P  S  L  N   M  G  L  A  T  .

CTCACACCCG ACCAATCAGA GAGCTCACTA AAATGCTAAT CAGGCAAAAA      700
     S  H  P   T  N  Q    R  A  H  .   N  A  N    Q  A  K  T
      H  T  R   P  I  R    E  L  T  K   M  L  I    R  Q  K
    L  T  P  D  Q  S  E    S  S  L    K  C  .    S  G  K  N
```

Fig. 5C

```
          10          20          30          40          50
     1234567890  1234567890  1234567890  1234567890  1234567890
     CAGGAGGTAA  AGCAATAGCC  AATCATCTAT  TGCCTGAGAG  CACAGCGGGA   750
       G G K     A I A N     H L L       P E S       T A G
      Q E V K    Q . P       I I Y       C L R A    Q R E
      R R .     S N S Q     S S I A     . E H S G K

AGGACAAGGA  TTGGGATATA  AACTCAGGCA  TTCAAGCCAG  CAACAGCAAC   800
       R T R    I G I .     T Q A       F K P A      T A T
      G Q G     L G Y K     L R H       S S Q      Q Q Q P
      D K D     W D I       N S G I    Q A S       N S N

CCCCTTTGGG  TCCCCTCCCA  TTGTATGGA   GCTCTGTTTT  CACTCTATTT   850
       P F G    S P P I     V W E       L C F      H S I S
      P L G     P L P       L Y G S     S V F      T L F
      P L W V   . P S H     C M G      A L F S     L Y F

CACTCTATTA  AATCATGCAA  CTGCACTCTT  CTGGTCCGTG  TTTTTTATGG   900
       L Y .    I M Q       L H S S     G P C       F L W
      H S I K    S C N       C T L      L V R V     F Y G
      T L L    N H A T      A L F      W S V       F F M A

CTCAAGCTGA  GCTTTTGTTC  GCCATCCACC  ACTGCTGTTT  GCCACCGTCA   950
       L K L S    F C S      P S T       T A V C     H R H
      S S .     A F V R      H P P      L L F      A T V T
      Q A E     L L F       A I H H    C C L       P P S

CAGACCCGCT  GCTGACTTCC  ATCCCTTTGG  ATCCAGCAGA  GTGTCCACTG   1000
       R P A    A D F H     P F G       S S R       V S T V
      D P L      L T S      I P L D    P A E        C P L
      Q T R C   . L P       S L W     I Q Q S      V H C

TGCTCCTGAT  CCAGCGAGGT  ACCCATTGCC  ACTCCCGATC  AGGCTAAAGG   1050
       L L I     Q R G      T H C H     S R S      G . R
      C S .     S S E V     P I A       T P D      Q A K G
      A P D     P A R Y     P L P      L P I       R L K A
```

Fig. 5D

```
         10         20         30         40         50
1234567890 1234567890 1234567890 1234567890 1234567890
CTTGCCATTG TTCCTGCATG GCTAAGTGCC TGGGTTTGTC CTAATAGAAC      1100
 L A I V   P A W   L S A   W V C   P N R T
 L P L   F L H G   . V P   G F V   L I E L
  C H C   S C M   A K C L   G L S   . . N

TGAACACTGG TCACTGGGTT CCATGGTTCT CTTCCATGAC CCACGGCTTC      1150
 E H W   S L G S   M V L   F H D   P R L L
 N T G   H W V   P W F S   S M T   H G F
 . T L V   T G F   H G S   L P . P   T A S

TAATAGAGCT ATAACACTCA CCGCATGGCC CAAGATTCCA TTCCTTGGTA      1200
 I E L   . H S   P H G P   R F H   S L V
 . . S Y   N T H   R M A   Q D S I   P W Y
 N R A   I T L T   A W P   K I P   F L G I

TCTGTGAGGC CAAGAACCCC AGGTCAGAGA ANGTGAGGCT TGCCACCATT      1250
 S V R P   R T P   G Q R   X . G L   P P F
 L . G   Q E P Q   V R E   X E A   C H H L
  C E A   K N P   R S E X   V R L   A T I

TGGGAAGTGG CCCACTGCCA TTTTGGTAGC GGCCCACCAC CATCTTGGGA      1300
 G K W   P T A I   L V A   A H H   H L G S
 G S G   P L P   F W . R   P T T   I L G
W E V A   H C H   F G S   G P P P   S W E

GCTGTGGGAG CAAGGATCCC CCAGTAACA                             1329
  C G S   K D P   P V T
A V G A   R I P   Q .
 L W E   Q G S P   S N
```

Fig. 6A

```
         10         20         30         40         50
1234567890 1234567890 1234567890 1234567890 1234567890
CCTAGAACGT ATTCTGGAGA ATTGGGACCA ATGTGACACT CAGACGCTAA      50
  P R T Y   S G E   L G P   M . H S   D A K
 L E R   I L E N   W D Q   C D T   Q T L R
  . N V   F W R   I G T N   V T L   R R .

GAAAGAAACG ATTTATATTC TTCTGCAGTA CCGCCTGGCC ACAATATCCT     100
  K E T   I Y I L   L Q Y   R L A   T I S S
   K K R   F I F   F C S T   A W P   Q Y P
 E R N D   L Y S   S A V   P P G   H N I L

CTTCAAGGGA GAGAAACCTG GCTTCCTGAG GGAAGTATAA ATTATAACAT     150
   S R E   R N L   A S . G   K Y K L   . H
 L Q G R   E T W   L P E   G S I N   Y N I
  F K G   E K P G   F L R   E V .   I I T S

CATCTTACAG CTAGACCTCT TCTGTAGAAA GGAGGGCAAA TGGAGTGAAG     200
  H L T A   R P L   . L . K   G G Q M   E . S
  I L Q . L D L F   C R K   E G K   W S E V
  S Y S . T S   S V E R   R A N   G V K

TGCCATATGT GCAAACTTTC TTTTCATTAA GAGACAACTC ACAATTATGT     250
  A I C   A N F L   F I K   R Q L   T I M .
  . P Y V   Q T F   F S L R   D N S   Q L C
  C H M C   K L S   F H .   E T T   H N Y V

AAAAAGTGTG GTTTATGCCC TACAGGAAGC CCTCAGAGTC CACCTCCCTA     300
   K V W   F M P   Y R K P   S E S   T S L
  K K C G   L C P   T G S   P Q S   P P Y
  K S V   V Y A L   Q E A   L R V   H L P T

CCCCAGCGTC CCCTCCCCGA CTCCTTCCTC AACTAATAAG GACCCCCTT     350
  P Q R P   L P D   S F L   N . . G   P P F
  P S V   P S P T   P S S   T N K   D P P L
  P A S   P P R   L L P Q   L I R   T P L

TAACCCAAAC GGTCCAAAAG GAGATAGACA AAGGGGTAAA CAATGAACCA     400
  N P N   G P K G   D R Q   R G K   Q . T K
  T Q T   V Q K   E I D K   G V N   N E P
  . P K R   S K R   R . T   K G .   T M N Q

AAGAGTGCCA ATATTCCCCG ATTATGCCCC CTCCAAGCAG TGAGGAGG     450
  E C Q   Y S P   I M P P   P S S   E R R
  K S A N   I P R   L C P   L Q A V   R G G
  R V P   I F P D   Y A P   S K Q   . E E E

AGAATTCGGC CCAGCCAGAG TGCCTGTACC TTTTTCTCTC TCAGACTTAA     500
  R I R P   S Q S   A C T   F F S L   R L K
  E F G   P A R V   P V P   F S L   S D L K
   N S A   Q P E   C L Y L   F L S   Q T .
```

Fig. 6B

```
           10         20         30         40         50
  1234567890 1234567890 1234567890 1234567890 1234567890
  AGCAAATTAA AATAGACCTA GGTAAATTCT CAGATAACCC TGACGGCTAT    550
   A  N  .   N  R  P  R   .  I  L  R  .  P   .  .  R  L  Y
     Q  I  K   I  D  L   G  K  F  S   D  N  P   D  G  Y
   S  K  L  K   .  T  .   V  N  S   Q  I  T  L   T  A  I

ATTGATGTTT TACAAGGGTT AGGACAATCC TTTGATCTGA CATGGAGAGA    600
   .  C  F   T  R  V   R  T  I  L   .  S  D   M  E  R
     I  D  V  L   Q  G  L   G  Q  S   F  D  L  T   W  R  D
   L  M  F   Y  K  G  .   D  N  P   L  I  .   H  G  E  I

TATAATGTTA CTACTAAATC AGACACTAAC CCCAAATGAG AGAAGTGCCG    650
   Y  N  V  T   T  K  S   D  T  N   P  K  .   E  K  C  R
     I  M  L   L  L  N  Q   T  L  T   P  N  E   R  S  A  A
   .  C  Y  Y   .  I  R  H   .  P   Q  M  R   E  V  P

CTGTAACTGC AGCCCGAGAG TTTGGCGATC TTTGGTATCT CAGTCAGGCC    700
   C  N  C   S  P  R  V   W  R  S   L  V  S   Q  S  G  Q
     V  T  A   A  R  E   F  G  D  L   W  Y  L   S  Q  A
   L  .  L  Q   P  E  S   L  A  I   F  G  I  S   V  R  P

AACAATAGGA TGACAACAGA GGAAAGAACA ACTCCCACAG CCAGCAGGC     750
   Q  .  D   D  N  R   G  K  N  N   S  H  R   P  A  G
     N  N  R  M   T  T  E   E  R  T   T  P  T  G   Q  Q  A
   T  I  G   .  Q  Q  R   K  E  Q   L  P  Q   A  S  R  Q

AGTTCCCAGT GTAGACCCTC ATTGGGACAC AGAATCAGAA CATGGAGATT    800
   S  S  Q  C   R  P  S   L  G  H   R  I  R  T   W  R  L
     V  P  S   V  D  P  H   W  D  T   E  S  E   H  G  D  W
   F  P  V   .  T  L   I  G  T  Q   N  Q  N   M  E  I

GGTGCCACAA ACATTTGCTA ACTTGCGTGC TAGAAGGACT GAGGAAAACT    850
   V  P  Q   T  F  A  N   L  R  A   R  R  T   E  E  N  .
     C  H  K   H  L  L   T  C  V  L   E  G  L   R  K  T
   G  A  T  N   I  C  .   L  A  C   .  K  D  .   G  K  L

AGGAAGAAGC CTATGAATTA CTCAATGATG TCCACTATAA CACAGGGAAA    900
   E  E  A   Y  E  L   L  N  D  V   H  Y  N   T  G  K
     R  K  K  P   M  N  Y   S  M  M   S  T  I  T   Q  G  K
   G  R  S   L  .  I  T   Q  .  C   P  L  .   H  R  E  R

GGAAGAAAAT CTTACTGCTT TTCTGGACAG ACTAAGGGAG GCATTGAGGA    950
   G  R  K  S   Y  C  F   S  G  Q   T  K  G  G   I  E  E
     E  E  N   L  T  A  F   L  D  R   L  R  E   A  L  R  K
   K  K  I   L  L  L   F  W  T  D   .  G  R   H  .  G

AGCATACCTC CCTGTCACCT GACTCTATTG AAGGCCAACT AATCTTAAAG   1000
   A  Y  L   P  V  T  .   L  Y  .   R  P  T   N  L  K  G
     H  T  S   L  S  P   D  S  I  E   G  Q  L   I  L  K
   S  I  P  P   C  H  L   T  L  L   K  A  N   .  S  .  R
```

Fig. 6C

```
              10         20         30         40         50
         1234567890 1234567890 1234567890 1234567890 1234567890
         GATAAGTTTA TCACTCAGTC AGCTGCAGAC ATTAGAAAAA ACTTCAAAAG   1050
          . V Y  H S V    S C R H  . K K  L Q K
          D K F I  T Q S A A D  I R K N  F K S
          . I S L  S L S Q  L Q T  L E K  T S K V

TCTGCCTTAG GCCCGGAGCA GAACTTAGAA ACCCTATTTA ACTTGGCATC   1100
          S A L G  P E Q  N L E  T L F N  L A S
          L P . A R S R T .  K  P Y L  T W H P
          C L R  P G A  E L R N  P I .  L G I

CTCAGTTTTT TATAATAGAG ATCAGGAGGA GCAGGCGAAA CGGGACAAAC   1150
          S V F  Y N R D  Q E E  Q A K  R D K R
          Q F F  I I E  I R R S  R R N  G T N
          L S F L  . . R  S G G  A G E T  G Q T

GGGATAAAAA AAAAAGGGGG GGTCCACTAC TTTAGTCATG GCCCTCAGGC   1200
          D K K  K R G  G P L L  . S W  P S G
          G I K K  K G G  V H Y  F S H G  P Q A
          G . K  K K G G  S T T  L V M  A L R Q

AAGCAGACTT TGGAGGCTCT GCAAAAGGGA AAAGCTGGGC AAATCAAATG   1250
          K Q T L .  E A L  Q K G  K A G Q  I K C
          S R L  W R L C  K R E  K L G  K S N A
          A D F  G G S  A K G K  S W A  N Q M

CCTAATAGGG CTGGCTTCCA GTGCGGTCTA CAAGGACACT TTAAAAAGA    1300
          L I G  L A S S A V Y  K D T  L K K I
          . . G  W L P  V R S T  R T L  . K R
          P N R A  G F Q  C G L  Q G H F  K K D

TTATCCAAGT AGAAATAAGC CGCCCCCTTG TCCATGCCCC TTACGTCAAG   1350
          I Q V  E I S  R P L V  H A P  Y V K
          L S K . K . A  A P L  S M P L  T S R
          Y P S  R N K P  P P C  P C P  L R Q G

GGAATCACTG GAAGGCCCAC TGCCCCAGGG GATGAAGATA CTCTGAGTCA   1400
          G I T G  R P T  A P G  D E D T  L S Q
          E S L  E G P L  P Q G  M K I  L . V R
          N H W  K A H  C P R G  . R Y  S E S

GAAGCCATTA ACAGATGAT CCAGCAGCAG GACTGAGGGT GCCCGGGGCG   1450
          K P L  T R . S  S S R  T E G  A R G E
          S H . P D D  P A A G  L R V  P G A
          E A I N  Q M I  Q Q Q  D . G C  P G R

AGCGCCAGCC CATGCCATCA CCCTCACAGA GCCCGGGTA TGTTTGACCA   1500
          R Q P  M P S  P S Q S  P G Y V  . P
          S A S P  C H H  P H R  A P G M  F D H
          A P A  H A I T  L T E  P R V  C L T I
```

Fig. 6D

```
          10         20         30         40         50
 1234567890 1234567890 1234567890 1234567890 1234567890
TTGAGAGCCA A                                                1511
 L  R   A
   . E  P
  E  S  Q
```

Fig. 7A

```
          10         20         30         40         50
 1234567890 1234567890 1234567890 1234567890 1234567890
ATGGGCAGCA GCCATCATCA TCATCATCAC AGCAGCGGCC TGGTGCCGCG      50
 M  G  S  S  H  H  H  H  H  H  S  S  G  L  V  P  R

CGGCAGCCAT ATGGCTAGCA TGACTGGTGG ACAGCAAATG GGTCGGATCC     100
 G  S  H  M  A  S  M  T  G  G  Q  Q  M  G  R  I  L

TAGAACGTAT TCTGGAGAAT TGGGACCAAT GTGACACTCA GACGCTAAGA     150
  E  R  I  L  E  N  W  D  Q  C  D  T  Q  T  L  R

AAGAAACGAT TTATATTCTT CTGCAGTACC GCCTGGCCAC AATATCCTCT     200
 K  K  R  F  I  F  F  C  S  T  A  W  P  Q  Y  P  L

TCAAGGAGA GAAACCTGGC TTCCTGAGGG AAGTATAAAT TATAACATCA      250
 Q  G  R  E  T  W  L  P  E  G  S  I  N  Y  N  I  I

TCTTACAGCT AGACCTCTTC TGTAGAAAGG AGGGCAAATG GAGTGAAGTG     300
  L  Q  L  D  L  F  C  R  K  E  G  K  W  S  E  V

CCATATGTGC AAACTTTCTT TTCATTAAGA GACAACTCAC AATTATGTAA     350
 P  Y  V  Q  T  F  F  S  L  R  D  N  S  Q  L  C  K

AAAGTGTGGT TTATGCCCTA CAGGAAGCCC TCAGAGTCCA CCTCCCTACC     400
 K  C  G  L  C  P  T  G  S  P  Q  S  P  P  P  Y  P

CCAGCGTCCC CTCCCCGACT CCTTCCTCAA CTAATAAGGA CCCCCCTTTA     450
  S  V  P  S  P  T  P  S  S  T  N  K  D  P  P  L

ACCCAAACGG TCCAAAAGGA GATAGACAAA GGGGTAAACA ATGAACCAAA     500
 T  Q  T  V  Q  K  E  I  D  K  G  V  N  N  E  P  K

GAGTGCCAAT ATTCCCCGAT TATGCCCCCT CCAAGCAGTG AGAGGAGGAG     550
 S  A  N  I  P  R  L  C  P  L  Q  A  V  R  G  G  E

AATTCGGCCC AGCCAGAGTG CCTGTACCTT TTTCTCTCTC AGACTTAAAG     600
 F  G  P  A  R  V  P  V  P  F  S  L  S  D  L  K

CAAATTAAAA TAGACCTAGG TAAATTCTCA GATAACCCTG ACGGCTATAT     650
 Q  I  K  I  D  L  G  K  F  S  D  N  P  D  G  Y  I

TGATGTTTTA CAAGGGTTAG GACAATCCTT TGATCTGACA TGGAGAGATA     700
  D  V  L  Q  G  L  G  Q  S  F  D  L  T  W  R  D  I

TAATGTTACT ACTAAATCAG ACACTAACCC CAAATGAGAG AAGTGCCGCT     750
  M  L  L  L  N  Q  T  L  T  P  N  E  R  S  A  A
```

GTAACTGCAG CCCGAGAGTT TGGCGATCTT TGGTATCTCA GTCAGGCCAA    800
       V  T  A  A  R  E  F   G  D  L   W  Y  L  S  Q  A  N

CAATAGGATG ACAACAGAGG AAAGAACAAC TCCCACAGGC CAGCAGGCAG    850
       N  R  M   T  T  E  E  R  T  T   P  T  G   Q  Q  A  V

TTCCCAGTGT AGACCCTCAT TGGACACAG AATCAGAACA TGGAGATTGG     900
        P  S  V   D  P  H   W  D  T  E   S  E  H   G  D  W

TGCCACAAAC ATTTGCTAAC TTGCGTGCTA GAAGGACTGA GGAAAACTAG    950
       C  H  K  H  L  L  T   C  V  L   E  G  L  R   K  T  R

GAAGAAGCCT ATGAATTACT CAATGATGTC CACTATAACA CAGGGAAAGG    1000
       K  K  P   M  N  Y  S   M  M  S   T  I  T   Q  G  K  E

AAGAAAATCT TACTGCTTTT CTGGACAGAC TAAGGGAGGC ATTGAGGAAG    1050
        E  N  L   T  A  F   L  D  R  L   R  E  A   L  R  K

CATACCTCCC TGTCACCTGA CTCTATTGAA GGCCAACTAA TCTTAAAGGA    1100
       H  T  S  L  S  P  D   S  I  E   G  Q  L   I  L  K  D

TAAGTTTATC ACTCAGTCAG CTGCAGACAT TAGAAAAAAC TTCAAAAGTC    1150
       K  F  I   T  Q  S  A   A  D  I   R  K  N   F  K  S  L

TGCCTAAGCT TGCGGCCGCA CTCGAGCACC ACCACCACCA CCACTGAGAT    1200
        P  K  L   A  A  A   L  E  H  H   H  H  H   H  .  D

CCGGCTGCTA ACAAAGCCCG AAAGGAAGCT GAGTTGGCTN GTGGCNA       1247
       P  A  A  N  K  A  R   K  E  A   E  L  A  X   G
```

Fig. 8A

```
          10         20         30         40         50
 1234567890 1234567890 1234567890 1234567890 1234567890
ATGGCTAGCA TGACTGGTGG ACAGCAAATG GGTCGGATCC TAGAACGTAT     50
 M  A  S  M  T  G  G   Q  Q  M   G  R  I  L  E  R  I

TCTGGAGAAT TGGGACCAAT GTGACACTCA GACGCTAAGA AAGAAACGAT    100
 L  E  N  W  D  Q  C   D  T  Q   T  L  R  K  K  R  F

TTATATTCTT CTGCAGTACC GCCTGGCCAC AATATCCTCT TCAAGGAGA     150
  I  F  F  C  S  T   A  W  P  Q   Y  P  L   Q  G  R

GAAACCTGGC TTCCTGAGGG AAGTATAAAT TATAACATCA TCTTACAGCT    200
 E  T  W  L  P  E  G   S  I  N   Y  N  I  I  L  Q  L

AGACCTCTTC TGTAGAAAGG AGGGCAAATG GAGTGAAGTG CCATATGTGC    250
 D  L  F   C  R  K   E  G  K  W   S  E  V   P  Y  V  Q

AAACTTTCTT TTCATTAAGA GACAACTCAC AATTATGTAA AAGTGTGGT     300
 T  F  F  S  L  R   D  N  S   Q  L  C  K   K  C  G

TTATGCCCTA CAGGAAGCCC TCAGAGTCCA CCTCCCTACC CCAGCGTCCC    350
 L  C  P  T   G  S  P   Q  S  P   P  P  Y  P   S  V  P

CTCCCCGACT CCTTCCTCAA CTAATAAGGA CCCCCCTTTA ACCCAAACGG    400
 S  P   T  P  S  S   T  N  K  D   P  P  L   T  Q  T  V

TCCAAAAGGA GATAGACAAA GGGGTAAACA ATGAACCAAA GAGTGCCAAT    450
 Q  K  E   I  D  K   G  V  N  N   E  P  K   S  A  N

ATTCCCCGAT TATGCCCCCT CCAAGCAGTG AGAGGAGGAG AATTCGGCCC    500
 I  P  R  L   C  P  L   Q  A  V   R  G  G   E  F  G  P

AGCCAGAGTG CCTGTACCTT TTCTCTCTC AGACTTAAAG CAAATTAAAA     550
 A  R  V   P  V  P  F   S  L  S   D  L  K   Q  I  K  I

TAGACCTAGG TAAATTCTCA GATAACCCTG ACGGCTATAT TGATGTTTTA    600
  D  L  G  K  F  S   D  N  P  D   G  Y  I   D  V  L

CAAGGGTTAG GACAATCCTT TGATCTGACA TGGAGAGATA TAATGTTACT    650
 Q  G  L  G  Q  S  F   D  L  T   W  R  D  I   M  L  L

ACTAAATCAG ACACTAACCC CAAATGAGAG AAGTGCCGCT GTAACTGCAG    700
 L  N  Q   T  L  T  P   N  E  R   S  A  A   V  T  A  A

CCCGAGAGTT TGGCGATCTT TGGTATCTCA GTCAGGCCAA CAATAGGATG    750
 R  E  F   G  D  L   W  Y  L  S   Q  A  N   N  R  M
```

ACAACAGAGG AAAGAACAAC TCCCACAGGC CAGCAGGCAG TTCCCAGTGT  800
 T  T  E  E   R  T  T    P  T  G    Q  Q  A  V   P  S  V

AGACCCTCAT TGGACACAG AATCAGAACA TGGAGATTGG TGCCACAAAC  850
 D  P  H   W  D  T  E    S  E  H   G  D  W   C  H  K  H

ATTTGCTAAC TTGCGTGCTA GAAGGACTGA GGAAAACTAG GAAGAAGCCT  900
  L  L  T   C  V  L    E  G  L  R    K  T  R   K  K  P

ATGAATTACT CAATGATGTC CACTATAACA CAGGGAAAGG AAGAAAATCT   950
 M  N  Y  S  M  M  S    T  I  T    Q  G  K  E   E  N  L

TACTGCTTTT CTGGACAGAC TAAGGGAGGC ATTGAGGAAG CATACCTCCC  1000
 T  A  F   L  D  R  L    R  E  A    L  R  K   H  T  S  L

TGTCACCTGA CTCTATTGAA GGCCAACTAA TCTTAAAGGA TAAGTTTATC  1050
  S  P  D   S  I  E    G  Q  L  I    L  K  D  K  F  I

ACTCAGTCAG CTGCAGACAT TAGAAAAAAC TTCAAAAGTC TGCCTAAGCT  1100
 T  Q  S  A   A  D  I   R  K  N    F  K  S  L   P  K  L

TGCGGCCGCA CTCGAGCACC ACCACCACCA CCACTGAGAT CCGGCTGCTA  1150
 A  A  A   L  E  H  H    H  H  H   H  .  D   P  A  A  N

ACAAAGCCCG AAAGGAAGCT GAGTTGGCTG GTGGCA  1186
 K  A  R   K  E  A    E  L  A  G   G

Fig. 9A

```
           10         20         30         40         50
     1234567890 1234567890 1234567890 1234567890 1234567890
     ────────────────────────────────────────────────────────
     TGTCCGCTGT GCTCCTGATC CAGCACAGGC GCCCATTGCC TCTCCCAATT       50
      C  P  L  C  S  .  S  S  T  G  A  H  C  L  S  Q  L
       V  R  C  A  P  D  P  A  Q  A  P  I  A  S  P  N  W
        S  A  V  L  L  I  Q  H  R  R  P  L  P  L  P  I

GGGCTAAAGG CTTGCCATTG TTCCTGCACA GCTAAGTGCC TGGGTTCATC      100
      G  .  R  L  A  I  V  P  A  Q  L  S  A  W  V  H  P
       A  K  G  L  P  L  F  L  H  S  .  V  P  G  F  I
        G  L  K  A  C  H  C  S  C  T  A  K  C  L  G  S  S

CTAATCGAGC TGAACACTAG TCACTGGGTT CCACGGTTCT CTTCCATGAC      150
      N  R  A  E  H  .  S  L  G  S  T  V  L  F  H  D
       L  I  E  L  N  T  S  H  W  V  P  R  F  S  S  M  T
        .  S  S  .  T  L  V  T  G  F  H  G  S  L  P  .  P

CCATGGCTTC TAATAGAGCT ATAACACTCA CTGCATGGTC CAAGATTCCA      200
      P  W  L  L  I  E  L  .  H  S  L  H  G  P  R  F  H
       H  G  F  .  .  S  Y  N  T  H  C  M  V  Q  D  S  I
        M  A  S  N  R  A  I  T  L  T  A  W  S  K  I  P

TTCCTTGGAA TCCGTGAGAC CAAGAACCCC AGGTCAGAGA ACACAAGGCT      250
      S  L  E  S  V  R  P  R  T  P  G  Q  R  T  Q  G  L
       P  W  N  P  .  D  Q  E  P  Q  V  R  E  H  K  A
        F  L  G  I  R  E  T  K  N  P  R  S  E  N  T  R  L

TGCCACCATG TTGGAAGCAG CCCACCACCA TTTTGGAAGC AGCCCGCCAC      300
      .  P  P  C  W  K  Q  P  T  T  I  L  E  A  A  R  H
       C  H  H  V  G  S  S  P  P  P  F  W  K  Q  P  A  T
        A  T  M  L  E  A  A  H  H  H  F  G  S  S  P  P  L

TATCTTGGGA GCTCTGGGAG CAAGGACCCC AGGTAACAAT TGGTGACCA       350
      Y  L  G  S  S  G  S  K  D  P  R  .  Q  F  G  D  H
       I  L  G  A  L  G  A  R  T  P  G  N  N  L  V  T  T
        S  W  E  L  W  E  Q  G  P  Q  V  T  I  W  .  P

CGAAGGGACC TGAATCCGCA ACCATGAAGG GATCTCCAAA GCAATTGGAA      400
      E  G  T  .  .  I  R  N  H  E  G  I  S  K  A  I  G  N
       K  G  P  E  S  A  T  M  K  G  S  P  K  Q  L  E
        R  R  D  L  N  P  Q  P  .  R  D  L  Q  S  N  W  K
```

Fig. 9B

```
          10         20         30         40         50
  1234567890 1234567890 1234567890 1234567890 1234567890
  ATGTTCCTCC CAAGGCAAAA ATGCCCCTAA GATGTATTCT GGAGAATTGG    450
    V  P  P   K  A  K    M  P  L   R  C  I  L   E  N  W
   M  F  L   P  R  Q  K   C  P  .   D  V  F  W   R  I  G
    C  S  S   Q  G  K  N   A  P  K   M  Y  S   G  E  L  G

GACCAATTTG ACCCTCAGAC AGTAAGAAAA AAATGACTTA TATTCTTCTG    500
    D  Q  F  D   P  Q  T   V  R  K   K  .  L  I   F  F  C
    T  N  L   T  L  R  Q   .  E  K   N  D  L   Y  S  S  A
     P  I  .   P  S  D   S  K  K   K  M  T  Y   I  L  L

CAGTACCGCC CTGGCACGA TATCCTCTTC AAGGGGAGA AACCTGGCCT      550
    S  T  A   L  A  T  I   S  S  S   R  G  R   N  L  A  S
    V  P  P   W  P  R   Y  P  L  Q   G  G  E   T  W  P
    Q  Y  R  P   G  H  D   I  L  F   K  G  E  K   P  G  L

CCTGAGGGAA GTATAAATTA TAACACCATC TTACAGCTAG ACCTGTTTTG    600
    .  G  K   Y  K  L   .  H  H  L   T  A  R   P  V  L
    P  E  G  S   I  N  Y   N  T  I   L  Q  D   L  F  C
    L  R  E  V   .  I  I   T  P  S   Y  S  .   T  C  F  V

TAGAAAAGGA GGCAAATGGA GTGAAGTGCC ATATTTACAA ACTTTCTTTT    650
    .  K  R  R   Q  M  E   .  S  A   I  F  T  N   F  L  F
    R  K  G   G  K  W  S   E  V  P   Y  L  Q   T  F  F  S
    E  K  E   A  N  G   V  K  C  H   I  Y  K   L  S  F

CATTAAAAGA CAACTCGCAA TTATGTTAAC AGTGTGATTT GTGTTCCTAC    700
    I  K  R   Q  L  A  I   M  L  T   V  .  F   V  F  L  H
    L  K  D   N  S  Q   L  C  .  Q   C  D  L   C  S  Y
    H  .  K  T   T  R  N   Y  V  N   S  V  I  C   V  P  T

ACGGAAGCCC TCAGATTCTA CTCCCCACCC CCGGCATCTC CCCTGAATCC    750
     G  S  P   Q  I  L   L  P  T  P   G  I  S   P  E  S
    T  E  A  L   R  F  Y   S  P  P   P  A  S  P   L  N  P
    R  K  P   S  D  S  T   P  H  P   R  H  L   P  .  I  P

CTCCCCAACT TATT                                          764
    L  P  N  L
     S  P  T   Y
      P  Q  L   I
```

Fig. 10A

```
          10         20         30         40         50
 1234567890 1234567890 1234567890 1234567890 1234567890
 TGTCCGCTGT GCTCCTGATC CAGCACAGGC GCCCATTGCC TCTCCCAATT    50
  C  P  L   C  S  .    S  T  G    A  H  C    L  S  Q  L
   V  R  C   A  P  D    P  A  Q    A  P  I    A  S  P  N  W
 S  A  V    L  L  I    Q  H  R  R    P  L  P    L  P  I

GGGCTAAAGG CTTGCCATTG TTCCTGCACA GCTAAGTGCC TGGGTTCATC    100
  G  .  R   L  A  I  V  P  A  Q    L  S  A    W  V  H  P
   A  K  G   L  P  L    F  L  H  S   .  V  P    G  F  I
 G  L  K  A    C  H  C    S  C  T    A  K  C    L  G  S  S

CTAATCGAGC TGAACACTAG TCACTGGGTT CCACGGTTCT CTTCCATGAC    150
  N  R  A   E  H  .    S  L  G  S    T  V  L    F  H  D
   L  I  E  L    N  T  S    H  W  V    P  R  F  S    S  M  T
 .  S  S   .  T  L  V    T  G  F    H  G  S    L  P  .  P

CCATGGCTTC TAATAGAGCT ATAACACTCA CTGCATGGTC CAAGATTCCA    200
  P  W  L  L   .I  E  L    .  H  S    L  H  G  P    R  F  H
   H  G  F    .  .  S  Y    N  T  H    C  M  V    Q  D  S  I
 M  A  S   N  R  A    I  T  L  T    A  W  S    K  I  P

TTCCTTGGAA TCCGTGAGAC CAAGAACCCC AGGTCAGAGA ACACAAGGCT    250
  S  L  E    S  V  R  P    R  T  P    G  Q  R    T  Q  G  L
   P  W  N   P  .  D    Q  E  P  Q    V  R  E    H  K  A
 F  L  G  I    R  E  T    K  N  P    R  S  E  N    T  R  L

TGCCACCATG TTGGAAGCAG CCCACCACCA TTTTGGAAGC GGCCCGCCAC    300
   P  P  C    W  K  Q    P  T  T  I    L  E  A    A  R  H
 C  H  H  V    G  S  S    P  P  P    F  W  K  R    P  A  T
  A  T  M    L  E  A  A    H  H  H    F  G  S    G  P  P  L

TATCTTGGGA GCTCTGGGAG CAAGGACCCC CAGGTAACAA TTTGGTGACC    350
  Y  L  G   S    S  G  S    K  D  P    Q  V  T  I   W  .  P
   I  L  G   A  L  G  A    R  T  P    R  .  Q    F  G  D  H
 S  W  E    L  W  E    Q  G  P  P    G  N  N    L  V  T

ACGAAGGGAC CTGAATCCGC AACCATGAAG GGATCTCCAA AGCAATTGGA    400
  R  R  D   L  N  P  Q    P  .  R    D  L  Q    S  N  W  K
   E  G  T    .  I  R    N  H  E    G  I  S  K    A  I  G
 T  K  G  P    E  S  A    T  M  K    G  S  P  K    Q  L  E
```

Fig. 10B

```
           10         20         30         40         50
     1234567890 1234567890 1234567890 1234567890 1234567890
     AATGTTCCTC CCAAGGCAAA AATGCCCCTA AGATGTATTC TGGAGAATTG    450
       C  S  S    Q  G  K    N  A  P    K  M  Y  S  G  E  L
       N  V  P  P  K  A  K    M  P  L    R  C  I  L  E  N  W
       M  F  L    P  R  Q  K    C  P  .    D  V  F    W  R  I  G

GGACCAATCT GACCCTCAGA CAGTAAGAAA AAAAATGACT TATATTCTTC    500
       G  P  I  .  P  S  D    S  K  K    K  N  D  L  Y  S  S
       D  Q  S    D  P  Q  T    V  R  K    K  M  T    Y  I  L  L
       T  N  L    T  L  R    Q  .  E  K  K  .  L    I  F  F

TGCAGTACCG CCTGGCCACG GATATCCTCT TCAAGGGGGA GAAACCTGGC    550
       A  V  P    P  G  H  G    Y  P  L    Q  G  G    E  T  W  P
       Q  Y  R    L  A  T    D  I  L  F    K  G  E    K  P  G
       C  S  T  A  W  P  R    I  S  S    S  R  G  R    N  L  A

CTCCTGAGGG AAGTATAAAT TATAACACCA TCTTACAGCT AGACCTGTTT    600
       P  E  G    S  I  N    Y  N  T  I    L  Q  L    D  L  F
       L  L  R  E  V  .  I    I  T  P    S  Y  S  .    T  C  F
       S  .  G    K  Y  K  L  .  H  H    L  T  A    R  P  V  L

TGTAGAAAAG GAGGCAAATG GAGTGAAGTG CCATATTTAC AAACTTTCTT    650
       C  R  K  G    G  K  W    S  E  V    P  Y  L  Q    T  F  F
       V  E  K    E  A  N  G    V  K  C    H  I  Y    K  L  S  F
       .  K  R    R  Q  M  E  .  S  A    I  F  T    N  F  L

TTCATTAAAA GACAACTGGC AATTATGTAA ACAGTGTGAT TTGTGTCCTA    700
       S  L  K    D  N  S  Q    L  C  K    Q  C  D    L  C  P  T
       H  .  K    T  T  R    N  Y  V  N    S  V  I    C  V  L
       F  I  K  R    Q  L  A    I  M  .    T  V  .  F    V  S  Y

CAGGAAGCCC TCAGATCTAC CTCCCTACCC CGGCATCTCC CTGACTCCTT    750
       G  S  P    Q  I  Y    L  P  T  P    A  S  P    .  L  L
       Q  E  A  L  R  S  T    S  L  P    R  H  L  P    D  S  F
       R  K  P    S  D  L  P    P  Y  P    G  I  S    L  T  P  S

CCCCAACTAA TAAGGACCCA CTTCAGCCCA AACAGTCCAA AAGGACATAG    800
       P  Q  L  I  R  T  H    F  S  P    N  S  P  K    G  H
       P  N  .  _.  G  P  T    S  A  Q    T  V  Q    K  D  I
       P  T  N    K  D  P    L  Q  P  K    Q  S  K    R  T  .
```

Fig. 11A

```
          10          20          30          40          50
  1234567890  1234567890  1234567890  1234567890  1234567890
  GGCATTGATA  GCACCCATCA  GATGGCCAAA  TCATTATTTA  CTGGACCAGG   50
   G  I  D    S  T  H  Q    M  A  K    S  L  F  T    G  P  G
    A  L  I    A  P  I  R    W  P  N    H  Y  L    L  D  Q  A
     H  .  .    H  P  S    D  G  Q  I    I  I  Y    W  T  R

CCTTTTCAAA  ACTATCAAGC  AGATAGGGCC  CGTGAAGCAT  GCCAAAGAAA  100
   L  F  K    T  I  K  Q    I  G  P    V  K  H    A  K  E  I
    F  S  K    L  S  S  R    .  G  P    .  S  M    P  K  K
     P  F  Q  N    Y  Q  A    D  R  A    R  E  A  C    Q  R  N

TAATCCCCTG  CCTTATCGCC  ATGTTCCTTC  AGGAGAACAA  AGAACAGGCC  150
   .  I  P  C    L  I  A    M  F  L  Q    E  N  K    E  Q  A
    .  S  P  A    L  S  P    C  S  F    R  R  T  K    N  R  P
     N  P  L    P  Y  R  H    V  P  S    G  E  Q    R  T  G  H

ATTACCCAGG  GGAAGACTGG  CAACTAGATT  TTACCCACAT  GGCCAAATGT  200
   I  T  Q  G    K  T  G    N  .  I    L  P  T  W    P  N  V
    L  P  R    G  R  L  A    T  R  F    Y  P  H    G  Q  M  S
     Y  P  G    E  D  W    Q  L  D  F    T  H  M    A  K  C

CAGGGATTTC  AGCATCTACT  AGTCTGGGCA  GATACTTTCA  CTGGTTGGGT  250
   R  D  F    S  I  Y  .    S  G  Q    I  L  S    L  V  G  W
    G  I  S    A  S  T    S  L  G  R    Y  F  H    W  L  G
     Q  G  F  Q    H  L  L    V  W  A    D  T  F  T    G  W  V

GGAGTCTTCT  CCTTGTAGGA  CAGAAAAGAC  CCAAGAGGTA  ATAAAGGCAC  300
   S  L  L    L  V  G    Q  K  R  P    K  R  .    .  R  H
    G  V  F  S    L  .  D    R  K  D    P  R  G  N    K  G  T
     E  S  S    P  C  R  T    E  K  T    Q  E  V    I  K  A  L

TAATGAAATA  ATTCCCAGAT  TGGACTTCC   CCCAGGATTA  CAGGGTGACA  350
   .  .  N  N    S  Q  I    W  T  S    P  R  I  T    G  .  Q
    N  E  I    I  P  R  F    G  L  P    P  G  L    Q  G  D  N
     M  K  .    F  P  D    L  D  F  P    Q  D  Y    R  V  T
```

```
ATGGCCCCGC TTTCAAGGCT GCAGTAACCC AGGGAGTATC CCAGGTGTTA    400
 W  P  R    F  Q  G    C  S  N  P  G  S  I   P  G  V  R
  G  P  A    F  K  A    V  T  Q    G  V  S    Q  V  L
 M  A  P  L   S  R  L   Q  .  P    R  E  Y  P  R  C  .

GGCATACAAT ATCACTTACA CTGTGCCTGG AGGCCACAAT CCTCCAGAAA    450
  H  T  I    S  L  T    L  C  L  E  A  T  I    L  Q  K
 G  I  Q  Y  H  L  H    C  A  W    R  P  Q  S   S  R  K
  A  Y  N    I  T  Y  T  V  P  G    G  H  N    P  P  E  K

AGTCAAGAAA ATGAATGAAA CACTCAAAGA TCTAAAAAAG CTAACCCAAG    500
 S  Q  E  N   E  .  N    T  Q  R    S  K  K  A  N  P  R
  V  K  K    M  N  E  T  L  K  D    L  K  K    L  T  Q  E
   S  R  K   .  M  K    H  S  K  I   .  K  S   .  P  K

AAACCCACAT TGCATGACCT GTTCTGTTGC CTATAACCTT ACTAAGAATC    550
 N  P  H    C  M  T  C   S  V  A    Y  N  L    T  K  N  P
  T  H  I  A  .  P     V  L  L  P   I  T  L    L  R  I
 K  P  T  L  H  D  L    F  C  C    L  .  P  Y  .  E  S

CATAACTATC CCCCAAAAAG CAGGACTTAG CCCATACGAG ATGCTATATG    600
  .  L  S    P  K  K    Q  D  L  A  H  T  R    C  Y  M
 H  N  Y  P   P  K  S    R  T  .    P  I  R  D  A  I  W
  I  T  I    P  Q  K  A  G  L  S    P  Y  E    M  L  Y  G

GATGGCCTTT CCTAACCAAT GACCTTGTGC TTGACTGAGA AATGGCCAAC    650
 D  G  L  S  .  P  M    T  L  C    L  T  E  K   W  P  T
  M  A  F    P  N  Q  .  P  C  A   .  L  R    N  G  Q  L
   W  P  F   L  T  N    D  L  V  L  D  .  E    M  A  N

TTAGTTGCAG ACATCACCTC CTTAGCCAAA TATCAACAAG TTCTTAAAAC    700
  .  L  Q    T  S  P  P  .  P  N    I  N  K    F  L  K  H
   S  C  R   H  H  L    L  S  Q  I   S  T  S    S  .  N
  L  V  A  D  I  T  S    L  A  K    Y  Q  Q  V  L  K  T
```

Fig. 11C

```
         10         20         30         40         50
1234567890 1234567890 1234567890 1234567890 1234567890
ATCACAGGGA ACCTGTCCCC GAGAGGAGGG AAAGGAACTA TTCCACCCTG      750
  H R E    P V P      E R R      R N Y      S T L
 I T G N    L S P      R G G      K G T I    P P W
  S Q G    T C P R    E E G      K E L      F H P G

GTGACATG                                                   758
V T
 . H
  D M
```

```
GGACCCGTAG TATGGGGTAA TCCCCTCCGG GAAACCAAGC CCCAGTACTC AGAGAAGAA ATAGAATGGG GAACCTCACG AGGACATGGT TTCCTCCCCT      100
 G  I  P  V  V   N  P  L  R   E  T  K  P   Q  Y  S   E  E  E   I  E  N  G   T  S  R   G  H  G   F  L  P  S       34

CAGGATGGCT AGCCACTGAA GAAGGAAAAA TACTTTTGCT GGAGCTAAC CAATGGAAAT TACTTAAAAC CCTTAAGCAA ACCTTCCACT TAGGCATTGA       200
 Q  D  G   W  L   A  T  E   E  G  K  I   L  L  L   A  A  N   Q  W  K  L   T  L  Q  Q   T  F  M  L   G  I  D      67

TAGCACCCAT CAGATAGCCA AATCATTATT TACTGGACCA GGGCTTTCA AAATATCAA GCAGATAGTC AGGGCCTGTG AGGTGCCAA AAGAAATAT        300
 S  T  M   Q  I  A  K   S  L  F   T  G  P   G  L  F  K   T  I  K   Q  I  V   R  A  G  E   V  G  Q   R  N  N     100

CCCTGCCTT ATGCCAAGC TCTTCAGGA GAACAAGAA CAGGGCAATTA CCCAAGAGAA GACTGGCAAC TAGATTTTAT CCACATGCCA AATCACAGG         400
 P  L  P  Y   R  Q  A   P  S  G   E  Q  R   T  G  N  Y   P  R  E   D  W  Q  L   D  P  I   H  M  P   K  S  Q  G   134

GATTTCAGTG TCTACTAGTC TGGTAGATA CTTTCACTGG CTGAGGGCTTA GTAGACAGA AAGTTCCAA GAGGTAATAA AGGACTAGT                   500
 F  Q  C   L  L  V   W  V  D  T   F  T  G   L  E  A   A  P  P  C   R  T  E   K  P  Q   E  V  I  K   A  L  V     167

TCATGAAGTA ATTCCAGAT TGGACTTCC CTGAGGCTTA CAGAGTGACA ATGGTCCTGC TTTCAAGGCC ACAGTAACCC AGGAGTATC CAGGCGTAA         600
 H  E  V   I  P  R  F   G  L  P   .  G  L   Q  S  D  N   G  P  A   F  K  A   T  V  T  Q   G  V  S   Q  A  L     200

GGTATAGAAT ATCACTACA CTGCACTTAG AGGCCCTAT AGGGCACAAT GGTTGAGAA ATGAAA ACAC TCAAACAGA TCTAAACAAG CTAACCAGG         700
 G  I  E  Y   H  L  H   C  T  .   R  P  Q  S   S  G  K   V  E  K   M  K  T  L   K  R  H   L  N  K   L  T  Q  R   234

AAACCCACT CCCATCCCTC GCTCTGTGT CTATAGCCCT ACTAAGAATC CAAAACTCTC CCCAAAAGGC AGGACTTAGC CCATACAGAA TGCTGTATGG       800
 T  H  L   A  W  S   A  L  L  S   I  A  L   L  R  I   Q  N  S  P   Q  K  A   G  L  S   P  Y  R  K   L  Y  G     267

ACGGTCCTTC CTAACCAATG ACCTTCTGT TGACCAAGAG AATGCCAACT TAGTTCAGA CATCACCTCC TAGTCAAGT ATCAACAAGT TCTAAAACA         900
 R  S  F   L  T  N  D   L  L  L   D  Q  E   M  A  N  L   V  A  D   I  T  S   L  A  R  Y   Q  Q  V   L  K  T     300

TTACAAGGAG CCTGTCCCG AGAGGAGGA AAAGAAATAT TACTTACCC AACTGGCT CTGATCATT TTGAATCAAGT GAGTGGAGTC CAGGAGATTTG        1000
 L  Q  G  A   C  P  R   E  E  G   K  E  I  F   H  P  G   V  M  V   L  V  K  S   L  P  S   M  S  P   S  L  D  T   334

CATCCTGGG AGGAACCTAC CCAGTCATT TACTATCCC AACTGGCGTT TGATACAT CCAGGAGTC CAGGAATGCT TTGATATCAT CACACCCTG           1100
 S  M  G   G  P  Y   P  V  I  L   S  I  P   T  A  V   K  V  A  G   V  E  S   M  I  H   H  T  R  I   K  P  W     367

GATACTGCCG AAGGAACCCG AAAATCCAGG GGACAAGGT AGCTATTTCT TTGAACCTCT AGAGGATCTG TGCCTGCTCT TCAAGCAACA ACCGTGA        1197
 I  L  P   K  E  P  E   N  P  G   D  N  A   S  Y  F  P   E  D  L   C  L  L   F  K  Q  Q   P                      398
```

Fig. 16

MULTIPLE SCLEROSIS-ASSOCIATED RETROVIRAL (MSRV) NUCLEIC ACIDS CORRESPONDING TO THE ENV REGION

BACKGROUND OF THE INVENTION

Multiple sclerosis (MS) is a demyelinizing disease of the central nervous system (CNS) of which the complete cause still remains unknown.

Numerous studies have supported the hypothesis for a viral etiology of the disease, but none of the known viruses tested has proved to be the causative agent tested for: a review of the viruses tested for in MS for many years has been carried out by E. Norrby and R. T. Johnson.

Recently, a retrovirus, different from the known human retroviruses, was isolated from patients suffering from MS. The authors were able to show that this retrovirus could be transmitted in vitro, that patients suffering from MS produced antibodies capable of recognizing proteins associated with the infection of the leptomeningeal cells by this retrovirus, and that the expression of the latter could be greatly stimulated by the immediate-early genes of some herpesviruses.

All these results argue in favor of the role in MS of at least one unknown retrovirus or of a virus having a reverse transcriptase (RT) activity which is detectable by the method published by H. Perron and termed "LM7-type RT" activity.

The studies by the applicant have made it possible to obtain two continuous cell lines infected with natural isolates obtained from two different patients suffering from MS, by a culture method as described in the document WO-A-93 20188, whose content is incorporated by reference into the present description. These two lines derived from cells of human choroid plexus, called LM7PC and PLI-2, were deposited at the E.C.A.C.C. on 22 Jul. 1992 and 8 Jan. 1993, respectively, under numbers 92 072201 and 93 010817, in accordance with the provisions of the Treaty of Budapest. Moreover, the viral isolates possessing an LM7-type RT activity have also been deposited at the E.C.A.C.C. under the overall name of "strains". The "strain" or isolate harbored by the PLI-2 line, called POL-2, was deposited at the E.C.A.C.C. on 22 Jul. 1992 under No. V92072202. The "strain" or isolate harbored by the LM7PC line, called MS7PG, was deposited at the E.C.A.C.C. on 8 Jan. 1993 under No. V93010816.

Using the above-mentioned cultures and isolates, characterized by biological and morphological criteria, efforts were then made to characterize the genetic material associated with the viral particles produced in these cultures.

The proportions of genome already characterized were used to develop molecular detection tests for the viral genome and immunoserological tests, using the amino acid sequences encoded by the nucleotide sequences of the viral genome, in order to detect the immune response directed against epitopes associated with the viral infection and/or expression.

These tools have already made it possible to confirm an association between MS and the expression of the sequences identified in the patents cited further on. However, the viral system discovered by the applicant is related to a complex retroviral system. Indeed, the sequences which are found to be encapsidated in the extracellular viral particles produced by the different cultures of cells of patients suffering from MS show clearly that there is co-encapsidation of retroviral genomes which are related but different from the "wild-type" retroviral genome which produces the infectious viral particles. This phenomenon was observed between replicative retroviruses and endogenous retroviruses belonging to the same family, or even heterologous retroviruses. The concept of endogenous retrovirus is very important in the context of our discovery because, in the case of MSRV-1, it has been observed that endogenous retroviral sequences comprising sequences homologous to the MSRV-1 genome exist in normal human DNA. The existence of endogenous retroviral elements (ERV) related to MSRV-1 through all or part of their genome explains the fact that the expression of the MSRV-1 retrovirus in human cells can interact with related endogenous sequences. These interactions are found in the case of pathogenic and/or infectious endogenous retroviruses (for example some ecotropic strains of the Murine Leukemia virus), in the case of exogenous retroviruses whose nucleotide sequence may be found partially or completely in the form of ERVs, in the genome of the host animal (e.g. mouse mammary tumor exogenous virus transmitted via milk). These interactions consist mainly of (i) a transactivation or co-activation of ERVs by the replicative retrovirus, (ii) an "illegitimate" encapsidation of related RNAs of ERVs, or of ERVs—or even of cellular RNAs—simply possessing compatible encapsidation sequences, into the retroviral particles produced by the expression of the replicative strain, which are sometimes transmissible and sometimes with an inherent pathogenicity, and (iii) relatively high recombinations between the co-encapsidated genomes, in particular in the reverse transcription phases, which lead to the formation of hybrid genomes, which are sometimes transmissible and sometimes with an inherent pathogenicity.

Thus, (i) various MSRV-1-related sequences have been found in purified viral particles; (ii) molecular analysis of the various regions of the MSRV-1 retroviral genome should be carried out by systematically analyzing the co-encapsidated, interfering and/or recombinant sequences which are generated by the infection and/or expression of MSRV-1; furthermore, some clones may have portions of defective sequences produced by the retroviral replication and the template and/or transcription errors caused by reverse transcriptase; (iii) the families of sequences related to the same retroviral genomic region are the supports for an overall diagnostic detection which may be optimized by the identification of invariable regions among the clones expressed and by the identification of reading frames responsible for the production of antigenic and/or pathogenic polypeptides which may only be produced by a portion, or even only one, of the clones expressed and under these conditions, the systematic analysis of the clones expressed in one region of a given gene makes it possible to evaluate the frequency of variation and/or recombination of the MSRV-1 genome in this region and to define the optimum sequences for the applications, in particular the diagnostic applications; (iv) the pathology caused by a retrovirus such as MRSV-1 may be a direct effect of its expression and of the proteins or peptides produced as a result, but also an effect of the activation, encapsidation, recombination of related or heterologous genomes and proteins or peptides produced as a result; thus, these genomes associated with the expression and/or infection by MSRV-1 are an integral part of the potential pathogenicity of this virus and therefore constitute diagnostic detection supports and particular therapeutic targets. Likewise, any agent which is associated with, or which is a cofactor for these interactions responsible for the pathogenicity in question, such as MSRV-2 or the gliotoxic factor described in the patent application published under the No. FR-2,716,198, can participate in the development of an overall and very effective strategy for therapeutic diagnosis, prognosis, monitoring and/or integrated therapy for MS in particular, but also for any other disease associated with the same agents.

In this context, a parallel discovery has been made in another autoimmune disease, rheumatoid arthritis (RA), which has been described in the French patent application published under the No. FR-2,731,356. This discovery shows that, by applying methodological approaches similar to those which were used in the studies by the applicant on MS, it has been possible to identify a retrovirus expressed in RA which shares the sequences described for MSRV-1 in MS and also the coexistence of an MSRV-2-associated sequence which is also described in MS. As regards MSRV-1, the sequences commonly detected in MS and RA relate to the pol and gag genes. On the basis of current knowledge, it is possible to combine the gag and pol sequences described with the MSRV-1 strains expressed in these two diseases.

The present patent application has as its object various results, supplementary in relation to those already protected by the French patent applications:

No. 92/04322 of 3 Apr. 1992, published under No. 2,689, 519;

No. 92/13447 of 3 Nov. 1992, published under No. 2,689, 521;

No. 92/13443 of 3 Nov. 1992, published under No. 2,689, 520;

No. 94/01529 of 4 Feb. 1994, published under No. 2,715, 936;

No. 94/01531 of 4 Feb. 1994, published under No. 2,715, 939;

No. 94/01530 of 4 Feb. 1994, published under No. 2,715, 938;

No. 94/01532 of 4 Feb. 1994, published under No. 2,715, 937;

No. 94/14322 of 24 Nov. 1994, published under No. 2,727, 428;

No. 94/15810 of 23 Dec. 1994, published under No. 2,728, 585; and

Patent Application WO 97/06260.

SUMMARY OF THE INVENTION

The present invention relates, first of all, to a nucleic material, which may consist of a retroviral material, in isolated or purified state, which may be understood or characterized in various ways:

it comprises a nucleotide sequence chosen from the group which consists of (i) the sequences SEQ ID NO: 4, SEQ ID NO: 6, SEQ ID NO: 9, SEQ ID NO: 12, SEQ ID NO: 16, SEQ ID NO: 21, SEQ ID NO: 30 and SEQ ID NO: 31; (ii) the sequences complementary to sequences (i); and (iii) the sequences equivalent to sequences (i) or (ii), in particular the sequences having, for every series of 100 contiguous monomers, at least 50%, and preferentially at least 70% homology with sequences (i) or (ii) respectively;

it encodes a polypeptide having, for every contiguous series of at least 30 amino acids, at least 50%, and preferably at least 70% homology with a peptide sequence chosen from the group which consists of SEQ ID NO: 5, SEQ ID NO: 7, SEQ ID NO: 10, SEQ ID NO: 13, SEQ ID NO: 25 and SEQ ID NO: 26;

its pol gene comprises a nucleotide sequence identical or equivalent to a sequence chosen from the group which consists of SEQ ID NO: 4, SEQ ID NO: 16 and their complementary sequences;

the 5' end of its pol gene starts at nucleotide 1419 of SEQ ID NO: 21;

its pol gene encodes a polypeptide having, for every contiguous series of at least 30 amino acids, at least 50%, and preferably at least 70% homology with the peptide sequence SEQ ID NO: 5;

the 3' end of its gag gene ends at nucleotide 1418 of SEQ ID NO: 21;

its env gene comprises a nucleotide sequence identical or equivalent to a sequence chosen from the group which consists of SEQ ID NO: 9, and its complementary sequences;

its env gene comprises a nucleotide sequence which starts at nucleotide 1 of SEQ ID NO: 9 and ends at nucleotide 233 of SEQ ID NO: 6;

its env gene encodes a polypeptide having, for every contiguous series of at least 30 amino acids, at least 50%, and preferably at least 70% homology with the sequence SEQ ID NO: 10;

the U3R region of its 3' LTR comprises a nucleotide sequence which ends at nucleotide 617 of SEQ ID NO: 6;

the RU5 region of its 5' LTR comprises a nucleotide sequence which starts at nucleotide 755 of SEQ ID NO: 12 and ends at nucleotide 337 of SEQ ID NO: 30 or SEQ ID NO: 31;

a retroviral nucleic material comprising a sequence which starts at nucleotide 755 of SEQ ID NO: 12 and which ends at nucleotide 617 of SEQ ID NO: 6;

the retroviral nucleic material as defined above is in particular associated with at least one autoimmune disease such as multiple sclerosis or rheumatoid arthritis.

The invention also relates to a nucleotide fragment which corresponds to at least one of the following definitions:

it comprises or consists of a nucleotide sequence chosen from the group which consists of (i) the sequences SEQ ID NO: 4, SEQ ID NO: 6, SEQ ID NO: 9, SEQ ID NO: 12, SEQ ID NO: 16, SEQ ID NO: 21, SEQ ID NO: 30 and SEQ ID NO: 31; (ii) the sequences complementary to sequences (i); and (iii) the sequences equivalent to sequences (i) or (ii), in particular the sequences having, for every series of 100 contiguous monomers, at least 50%, and preferentially at least 70% homology with sequences (i) or (ii) respectively;

it comprises or consists of a nucleotide sequence encoding a polypeptide having, for every contiguous series of at least 30 amino acids, at least 50%, and preferably at least 70% homology with a peptide sequence chosen from the group which consists of SEQ ID NO: 5, SEQ ID NO: 7, SEQ ID NO: 10, SEQ ID NO: 13, SEQ ID NO: 25 and SEQ ID NO: 26.

Other subjects of the present invention are the following:

a nucleic probe for the detection of a retrovirus associated with multiple sclerosis and/or rheumatoid arthritis, capable of hybridizing specifically with any fragment defined above and belonging to the genome of said retrovirus; it advantageously possesses from 10 to 100 nucleotides, preferably from 10 to 30 nucleotides;

a primer for the amplification, by polymerization, of an RNA or of a DNA of a retrovirus associated with multiple sclerosis and/or rheumatoid arthritis, which comprises a nucleotide sequence identical or equivalent to at least a portion of the nucleotide sequence of a fragment defined above, in particular a nucleotide sequence having, for every series of 10 contiguous monomers, at least 50%, preferably at least 70% homology with at least said portion of said fragment; preferably the nucleotide sequence of a primer of the invention is chosen from SEQ ID NO: 8, SEQ ID NO: 11, SEQ ID NO: 14, SEQ ID NO: 15, SEQ ID NO: 17, SEQ ID NO: 18, SEQ ID NO: 19, SEQ ID NO: 20, SEQ ID NO: 23, and SEQ ID NO: 24;

an RNA or a DNA and in particular a replication and/or expression vector, comprising a genomic fragment of the nucleic material or a fragment defined above;

a peptide encoded by any open reading frame belonging to a nucleotide fragment defined above, in particular a polypeptide, for example oligopeptide forming or comprising an antigenic determinant recognized by sera of patients infected with the MSRV-1 virus, and/or in whom the MSRV-1 virus has been reactivated; a preferential peptide comprises a sequence identical, partially or completely, or equivalent to a sequence chosen from SEQ ID NO: 5, SEQ ID NO: 7, SEQ ID NO: 10, SEQ ID NO: 13, SEQ ID NO: 25 and SEQ ID NO: 26;

a diagnostic, prophylactic or therapeutic composition, in particular for inhibiting the expression of at least one retrovirus associated with multiple sclerosis and/or rheumatoid arthritis, comprising a nucleotide fragment defined above;

a method for detecting a retrovirus associated with multiple sclerosis and/or rheumatoid arthritis, in a biological sample, comprising the steps consisting of bringing an RNA and/or a DNA assumed to belong to or obtained from said retrovirus, or their complementary RNA and/or DNA, into contact with a composition comprising a nucleotide fragment defined above.

DEFINITIONS

Before detailing the invention, various terms used in the description and the claims are now defined.

Strain or isolate is understood to mean any infectious and/or pathogenic biological fraction containing, for example, viruses and/or bacteria and/or parasites, generating a pathogenic and/or antigenic power, harbored by a culture or a live host; by way of example, a viral strain according to the preceding definition may contain a co-infectious agent, for example a pathogenic protist.

The term "MSRV" used in the present description designates any pathogenic and/or infectious agent, as associated with MS, in particular a viral species, the attenuated strains of said viral species, or the interfering defective particles or particles containing co-encapsidated genomes or alternatively genomes recombined with a portion of the MSRV-1 genome, which are derived from this species. It is known that viruses and particularly viruses containing RNA exhibit variability, following in particular relatively high rates of spontaneous mutation, which will be taken into account below to define the concept of equivalence.

Human virus is understood to mean a virus capable of infecting or of being harbored by human beings.

Given all the natural or induced variations and/or recombination which may be encountered in practice in the present invention, the objects thereof, defined above and in the claims, have been expressed by comprising the equivalents or derivatives of the various biological materials defined below, in particular homologous nucleotide or peptide sequences.

The variant of a virus or of a pathogenic and/or infectious agent according to the invention comprises at least one antigen recognized by at least one antibody directed against at least one corresponding antigen of said virus and/or of said pathogenic and/or infectious agent, and/or a genome in which any portion is detected by at least one hybridization probe, and/or at least one nucleotide amplification primer specific for said virus and/or pathogenic and/or infectious agent, under defined hybridization conditions well known to persons skilled in the art.

According to the invention, a nucleotide fragment or an oligonucleotide or a polynucleotide is a stretch of monomers, or a biopolymer, characterized by the informational sequence of the natural nucleic acids, which is capable of hybridizing to any other nucleotide fragment under predefined conditions, it being possible for the stretch to contain monomers of different chemical structures and to be obtained from a natural nucleic acid molecule and/or by genetic recombination and/or by chemical synthesis; a nucleotide fragment may be identical to a genomic fragment of the MSRV-1 virus considered by the present invention, in particular a gene of the latter, for example pol or env in the case of said virus.

Thus, a monomer may be a natural nucleic acid nucleotide in which the constituent components are a sugar, a phosphate group and a nitrogen base; in RNA, the sugar is ribose; in DNA, the sugar is 2-deoxyribose; depending on whether DNA or RNA is involved, the nitrogen base is chosen from adenine, guanine, uracil, cytosine, thymine; or the nucleotide may be modified in at least one of the three constituent components; by way of example, the modification may occur at the level of the bases, generating modified bases such as inosine, 5-methyl-deoxycytidine, deoxyuridine, 5-dimethylaminodeoxyuridine, 2,6-diaminopurine, 5-bromodeoxyuridine and any other modified base promoting hybridization; at the level of the sugar, the modification may consist in the replacement of at least one deoxyribose with a polyamide, and at the level of the phosphate group, the modification may consist in its replacement with esters, in particular chosen from the esters of diphosphate, of alkyl and arylphosphonate and of phosphorothioate.

"Informational sequence" is understood to mean any ordered series of monomers, whose chemical nature and in which the order in a reference direction, constitute or otherwise a functional information of the same quality as that for the natural nucleic acids.

Hybridization is understood to mean the process during which, under appropriate operating conditions, two nucleotide fragments, having sufficiently complementary sequences, become annealed to form a complex, in particular a double or triple, structure, preferably in helical form.

A probe comprises a nucleotide fragment synthesized by the chemical route or obtained by digestion or enzymatic cleavage of a longer nucleotide fragment, comprising at least six monomers, advantageously from 10 to 100 monomers, preferably 10 to 30 monomers, and possessing a hybridization specificity under defined conditions; preferably, a probe possessing less than 10 monomers is not used alone, but is used in the presence of other probes which are equally short in length or otherwise; under certain specific conditions, it may be useful to use probes which are greater than 100 monomers in size; a probe may be used in particular for diagnostic purposes, and it may be, for example, capture and/or detection probes.

The capture probe may be immobilized on a solid support by any appropriate means, that is to say directly or indirectly, for example by covalent bonding or passive adsorption.

The detection probe may be labeled by means of a marker chosen in particular from radioactive isotopes, enzymes chosen in particular from peroxidase and alkaline phosphatase and those capable of hydrolyzing a chromogenic, fluorigenic or luminescent substrate, chromophoric chemical compounds, chromogenic, fluorigenic or luminescent compounds, analogs of nucleotide bases, and biotin.

The probes used for diagnostic purposes of the invention may be used in all known hybridization techniques, and in particular the so-called "DOT-BLOT" technique, "SOUTHERN BLOT" technique, "NORTHERN BLOT" technique which is a technique identical to the "SOUTHERN BLOT" technique but which uses RNA as target, the SANDWICH technique; advantageously, the SANDWICH technique is used in the present invention, comprising a specific capture probe and/or a specific detection probe, it being understood that the capture probe and the detection probe must have a nucleotide sequence which is at least partially different.

Any probe according to the present invention may hybridize in vivo or in vitro with the RNA and/or with the DNA, in order to block the replication, in particular translation and/or transcription, phenomena and/or to degrade said DNA and/or RNA.

A primer is a probe comprising at least six monomers, and advantageously from 10 to 30 monomers, possessing hybridization specificity under defined conditions, for the initiation of an enzymatic polymerization, for example in an amplification technique such as PCR (Polymerase Chain Reaction), in an extension method such as sequencing, in a reverse transcription method and the like.

Two nucleotide or peptide sequences are said to be equivalent or derived with respect to each other, or with respect to a reference sequence, if functionally the corresponding biopolymers can play substantially the same role, without being identical, in relation to the application or use considered, or in the technique in which they are involved; particularly equivalent are two sequences obtained because of the natural variability, in particular spontaneous mutation, of the species from which they were identified, or induced mutation, as well as two homologous sequences, the homology being defined below.

"Variability" is understood to mean any spontaneous or induced modification of a sequence, in particular by substitution, and/or insertion, and/or deletion of nucleotides and/or of nucleotide fragments, and/or extension and/or shortening of the sequence at least at one of the ends; a nonnatural variability may result from the genetic engineering techniques used, for example from the choice of the degenerate or nondegenerate synthetic primers selected to amplify a nucleic acid; this variability may result in modifications of any starting sequence, considered as a reference, and which may be expressed by a degree of homology with respect to said reference sequence.

Homology characterizes the degree of identity of two compared nucleotide or peptide fragments; it is measured by the percentage identity which is in particular determined by direct comparison of nucleotide or peptide sequences, with respect to reference nucleotide or peptide sequences.

Any nucleotide fragment is said to be equivalent to or derived from a reference fragment if it has a nucleotide sequence equivalent to the sequence of the reference fragment; according to the preceding definition, in particular equivalent to a reference nucleotide fragment are:

(a) any fragment capable of hybridizing, at least partially, with the complementary to the reference fragment, (b) any fragment whose alignment with the reference fragment leads to the identification of identical contiguous bases, in a greater number than with any other fragment obtained from another taxonomic group, (c) any fragment resulting or capable of resulting from the natural variability of the species from which it is obtained, (d) any fragment which may result from genetic engineering techniques applied to the reference fragment, (e) any fragment, containing at least eight contiguous nucleotides, encoding a peptide homologous or identical to the peptide encoded by the reference fragment, (f) any fragment different from the reference fragment through insertion, deletion, substitution of at least one monomer, extension, or shortening at least at one of its ends; for example, any fragment corresponding to the reference fragment, flanked at least at one of its ends by a nucleotide sequence not encoding a polypeptide.

Polypeptide is understood to mean in particular any peptide of at least two amino acids, in particular oligopeptide, protein, extracted, separated, or substantially isolated or synthesized, through the involvement of humans, in particular those obtained by chemical synthesis, or through expression in a recombinant organism.

Polypeptide partially encoded by a nucleotide fragment is understood to mean a polypeptide having at least three amino acids encoded by at least nine contiguous monomers included in said nucleotide fragment.

An amino acid is said to be analogous to another amino acid when their respective physicochemical characteristics, such as polarity, hydrophobicity and/or basicity, and/or acidity, and/or neutrality, are substantially the same; thus, a leucine is analogous to an isoleucine.

Any polypeptide is said to be equivalent to or derived from a reference polypeptide if the polypeptides compared have substantially the same properties, and in particular the same antigenic, immunological, enzymatic and/or molecular recognition properties; in particular equivalent to a reference polypeptide is:

(a) any polypeptide possessing a sequence in which at least one amino acid has been replaced by an analogous amino acid, (b) any polypeptide having an equivalent peptide sequence, obtained by natural or induced variation of said reference polypeptide, and/or of the nucleotide fragment encoding said polypeptide, (c) a mimotope of said reference polypeptide, (d) any polypeptide from whose sequence one or more amino acids of the L series are replaced by an amino acid of the D series, and vice versa, (e) any polypeptide into whose sequence a modification of the side chains of the amino acids has been introduced, such as for example an acetylation of the amine-containing functions, a carboxylation of the thiol functions, an esterification of the carboxyl functions, (f) any polypeptide in whose sequence one or more peptide bonds have been modified, such as for example the carba, retro, inverso, retro-inverso, reduced, and methylene-oxy bonds, (g) any polypeptide in which at least one antigen is recognized by an antibody directed against a reference polypeptide.

The percentage identity characterizing the homology between two peptide fragments compared is according to the present invention at least 50% and preferably at least 70%.

Given that a virus possessing a reverse transcriptase enzymatic activity may be genetically characterized both in RNA and DNA form, both the viral DNA and RNA will be mentioned in order to characterize the sequences relative to a virus possessing such a reverse transcriptase activity, termed MSRV-1 according to the present description.

The expressions of order which are used in the present description and the claims, such as "first nucleotide sequence", are not selected to express a particular order, but to define the invention more clearly.

Detection of a substance or agent is understood below to mean an identification, a quantification or a separation or isolation of said substance or of said agent.

BRIEF DESCRIPTION OF THE DRAWINGS

The invention will be understood more clearly on reading the detailed description which follows which is made with reference to the appended Figures.

FIG. 2 represents the nucleotide sequence of the clone called CL6-5' (SEQ ID NO: 4) and three potential reading frames in amino acids presented under the nucleotide sequence.

FIG. 3 represents the nucleotide sequence of the clone called CL6-3' (SEQ ID NO: 6) and three potential reading frames in amino acids presented under the nucleotide sequence.

FIG. 4 represents the nucleotide sequence of the clone called C15 (SEQ ID NO: 9) and three potential reading frames in amino acids presented under the nucleotide sequence.

FIG. 5 represents the nucleotide sequence of the clone called 5M6 (SEQ ID NO: 12) and three potential reading frames in amino acids presented under the nucleotide sequence.

FIG. 6 represents the nucleotide sequence of the clone called CL2 (SEQ ID NO: 21) and three potential reading frames in amino acids presented under the nucleotide sequence.

FIG. 7 represents a potential reading frame in amino acids expressed by pET28C-clone 2 (SEQ ID NO: 40) and presented under the nucleotide sequence.

FIG. 8 represents a potential reading frame in amino acids expressed by pET21C-clone 2 (SEQ ID NO: 41) and presented under the nucleotide sequence.

FIG. 9 represents the nucleotide sequence of the clone called LB13 (SEQ ID NO: 30) and three potential reading frames in amino acids presented under the nucleotide sequence.

FIG. 10 represents the nucleotide sequence of the clone called LA15 (SEQ ID NO: 31) and three potential reading frames in amino acids presented under the nucleotide sequence.

FIG. 11 represents the nucleotide sequence of the clone called LB16 (SEQ ID NO: 16) and three potential reading frames in amino acids presented under the nucleotide sequence.

FIG. 13 represents the MSRV1 env and 3' LTR sequences (which together form SEQ ID NO: 42). The horizontal arrows indicate the start of the env, U3 and R regions. In the env region, the signal peptide and the potential immunosuppressive region are underlined, the potential glycosilation sites are boxed and the potential cleavage sites are indicated by vertical arrows. In the U3R region: the regulatory element CART and the TATA Box are underlined, the "cap" site and the polyadenylation signal are also indicated.

FIG. 14 represents the 5' LTR (RU5) region followed by a PBS site (primer binding site) complementary to the Trp tRNA and by a gag gene encoding a protein of about 487 amino acids (which together form SEQ ID NO: 43). The amino acids conserved in the nucleocapsid are underlined twice. The amino acids defining the region of greatest homology in the capsid are in bold and underlined once. The / symbols in the amino acid sequence indicate variations observed depending on the clones and, in the nucleotide sequence, they indicate frame jumps in some clones. The boxed regions correspond to epitopes identified by peptide analysis of the C-terminal region.

FIG. 15 represents the integrase region of MSRV1 (SEQ ID NO: 44), the nucleotide sequence and the amino acid sequence deduced from the integrase region corresponding to clone 87-23. In FIG. 15, // means a frame jump which has been suppressed in order to restore the potential ORF. The letters in underlined bold characters represent the conserved amino acids in the retroviral integrases.

FIG. 16 describes the nucleotide and peptide sequences of clone B13 (identical to clone FBd13 described in previous applications) with indication of the ORFs and stop codons represented by a dot (SEQ ID NO: 45). The underlined region in bold represents the potential immunosuppressive domain. The single underlined domain represents the start of the 3' LTR.

DETAILED DESCRIPTION OF PREFERRED EMBODIMENTS

Example 1

Figure 1:
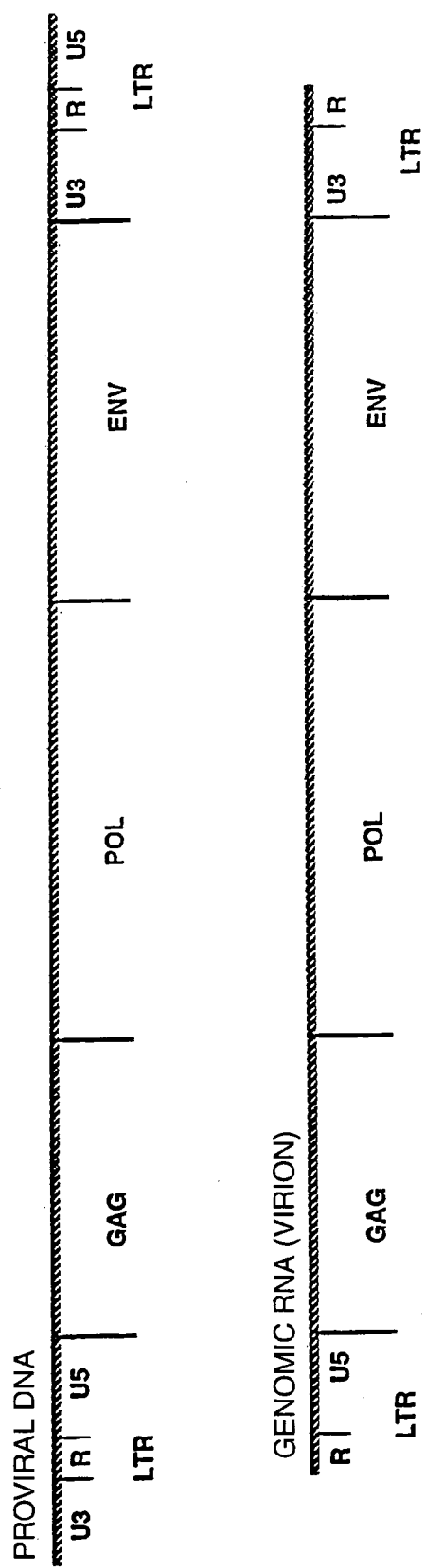
FIG. 1 represents the general structure of the proviral DNA and the genomic RNA of MSRV-1.

Preparation of a CL6-5' Region Encoding the N-Terminal End of Integrase and of a CL6-3' Region Containing the 3' Terminal Sequence of the MSRV-1 Genome A 3' RACE was carried out on the total RNA extracted from plasma from a patient suffering from MS. A healthy control plasma, treated under the same conditions, was used as negative control. The synthesis of cDNA was carried out with an oligo dT primer identified by SEQ ID NO: 1 (5' GAC TCG CTG CAG ATC GAT TTT TTT TTT TTT TTT T 3') and the reverse transcriptase "Expand™ RT" from Boehringer according to the conditions recommended by the company. A PCR was carried out with the enzyme Klentaq (Clontech) under the following conditions: 94° C. 5 min then 93° C. 1 min, 58° C. 1 min, 68° C. 3 min over 40 cycles and 68° C. for 8 min, with a final reaction volume of 50

Primers used for the PCR:

5' primer, identified by SEQ ID NO: 2

5' GCC ATC AAG CCA CCC AAG AAC TCT AAA CTT 3';

3' primer, identified by SEQ ID NO: 1

A second so-called "seminested" PCR was carried out with a 5' primer situated inside the region already amplified. This second PCR was carried out under the same experimental conditions as those used for the first PCR, using 10 gl of the amplification product derived from the first PCR.

Primers used for the seminested PCR:

5' primer, identified by SEQ ID NO: 3

5' CCA ATA GCC AGA CCA TTA TAT ACA CTA ATT 3';

3' primer, identified by SEQ ID NO: 1

The primers SEQ ID NO: 2 and SEQ ID NO: 3 are specific for the pol region of MRSV-1.

An amplification product of 1.9 Kb was obtained for the plasma of the MS patient. The corresponding fragment was not observed for the healthy control plasma. This amplification product was cloned in the following manner:

The amplified DNA was inserted into a plasmid with the aid of the TA Cloning Kit®. The 2 μl of DNA solution were mixed with 5 µl of sterile distilled water, 1 µl of a 10 times concentrated ligation buffer "10× LIGATION BUFFER", 2 µl of "pCR™ VECTOR" (25 ng/ml) and 1 gl of "T4 DNA LIGASE". This mixture was incubated overnight at 12° C. The next steps were carried out in accordance with the instructions for the TA Cloning kite (Invitrogen). At the end of the procedure, the white colonies of recombinant bacteria (white) were subcultured so as to be cultured and allow the extraction of the plasmids incorporated according to the so-called "miniprep" procedure. The plasmid preparation of each recombinant colony was cut with an appropriate restriction enzyme and analyzed on agarose gel. The plasmids possessing an insert detected under UV light after staining the gel with ethidium bromide were selected for the sequencing of the insert after hybridization with a primer complementary to the Sp6 promoter present on the cloning plasmid of the TA cloning Kit®. The reaction prior to the sequencing was then carried out according to the method recommended for using the sequencing kit "PRISM™ Ready Reaction AmpliTaq° FS, DyeDeoxy™ Terminator" (Applied Biosystems, ref. 402119) and the automated sequencing was carried out on the Applied Biosystems 373 A and 377 apparatus, according to the manufacturer's instructions.

The clone obtained contains a CL6-5' region encoding the N-terminal end of integrase and a CL6-3' region corresponding to the 3' terminal region of MSRV-1 and making it possible to define the end of the envelope (234 bp) and the U3 and R (401 bp) regions of the MSRV1 retrovirus.

The region corresponding to the N-terminal end of integrase is represented by its nucleotide sequence (SEQ ID NO: 4) in FIG. 2. The three potential reading frames are presented by their amino acid sequence under the nucleotide sequence, and the amino acid sequence of the N-terminal end of integrase is identified by SEQ ID NO: 5.

The C16-3' region is represented by its nucleotide sequence (SEQ ID NO: 6) in FIG. 3. The three potential reading frames are presented by their amino acid sequence under the nucleotide sequence. An amino acid sequence corresponding to the C-terminal end of the MSRV-1 env protein is identified by SEQ ID NO: 7.

Figure 12:
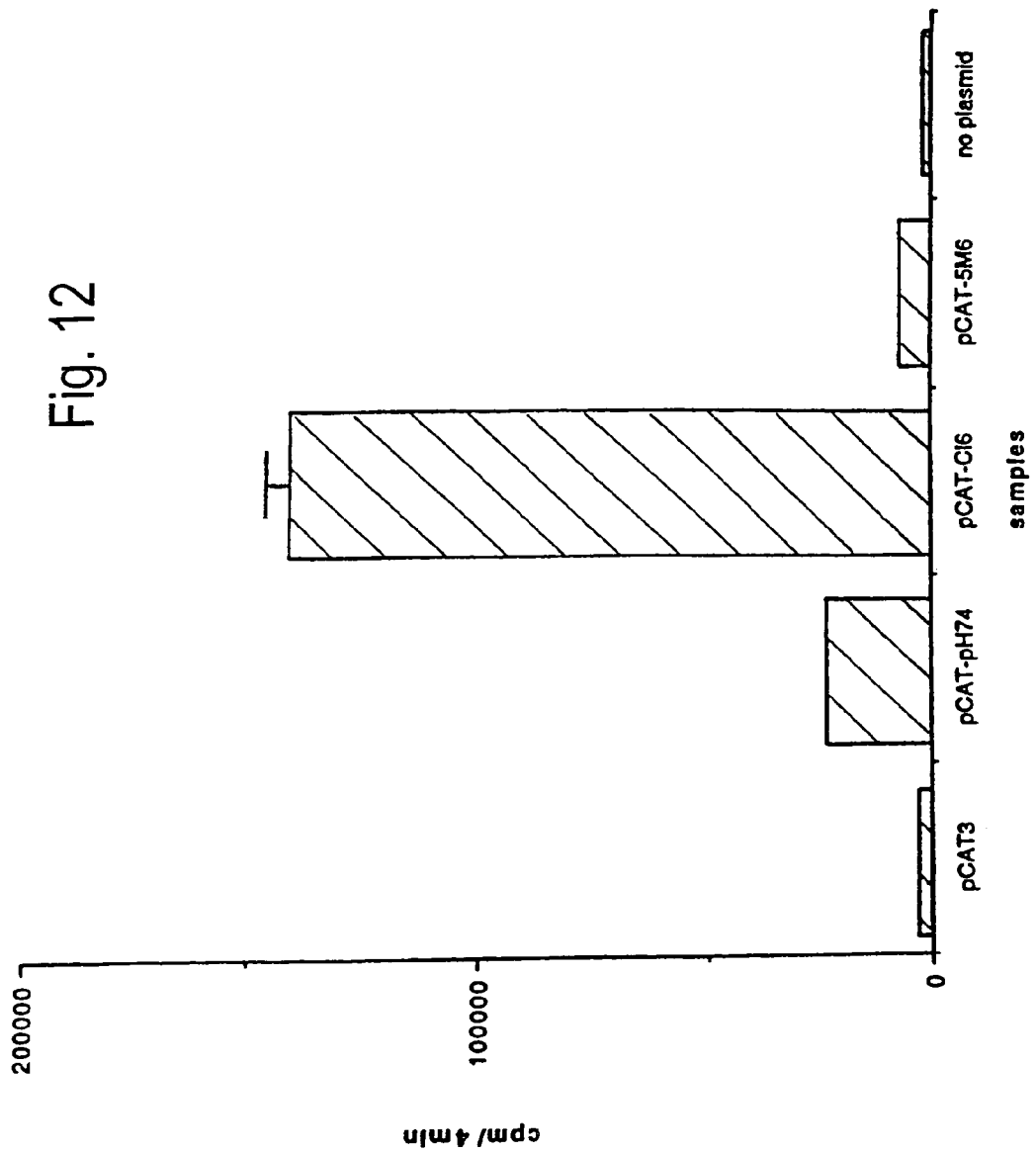
FIG. 12 represents the promoter activity expressed in cpm/4 min of the U3R sequences subcloned from LTRs of different origins into the plasmid PCAT3. PCAT3 means plasmid alone, PCAT-PH74 means plasmid plus endogenous U3R clone expressed in the placenta, PCATc16 means plasmid plus U3R clone amplified in the RNA of an MS plasma, PCAT-5M6 means plasmid plus U3R region amplified in the cellular DNA, "no plasmid" means absence of plasmid in the test.

In order to evaluate the promoter activity of the LTR obtained from clone 6 (c16), a test of promoter activity using the enzyme CAT (chloramphenicol acetyl transferase) was carried out with the corresponding U3R region. In parallel, a clone containing the same U3R region of endogenous retroviral RNA expressed in normal placenta (PH74) and a clone (5M6) obtained from DNA were tested. The result presented in FIG. 12 shows a very high promoter activity of the LTR derived from MS plasma (c16) and a significantly much lower activity with the sequences of non-MS endogenous origin.

Example 2

Preparation of the C15 Clone Containing the Region Encoding a Portion of the MSRV-1 Retrovirus Envelope A RT-PCR was carried out on the total RNA extracted from virions concentrated by ultra-centrifugation of a synoviocyte culture supernatant obtained from an MS patient. The synthesis of cDNA was carried out with an oligo dT primer and the reverse transcriptase "Expand™ RT" from Boehringer according to the conditions recommended by the company. A PCR was carried out with the Expand™ Long Template PCR System (Boehringer) under the following conditions: 94° C. 5 min then 93° C. 1 min, 60° C. 1 min, 68° C. 3 min over 40 cycles and 68° C. for 8 min and with a final reaction volume of 50 µl.

Primers used for the PCR:

5' primer, identified by SEQ ID NO: 2

5' GCC ATC AAG CCA CCC AAG AAC TCT TAA CTT 3';

3' primer, identified by SEQ ID NO: 8
5' TGG GGT TCC ATT TGT AAG ACC ATC TGT AGC TT 3'

A second so-called "seminested" PCR was carried out with a 5' primer situated inside the region already amplified. This second PCR was carried out under the same experimental conditions as those used for the first PCR (except that 30 cycles were used instead of 40), using 10 µl of the amplification product derived from the first PCR.

Primers used for the seminested PCR:

5' primer, identified by SEQ ID NO: 3

5' CCA ATA GCC AGA CCA TTA TAT ACA CTA ATT 3';

3' primer, identified by SEQ ID NO: 8

The primers SEQ ID NO: 2 and SEQ ID NO: 3 are specific for the pol region of MRSV-1. The primer SEQ ID NO: 8 is specific for the sequence FBd13 (also called B13) and is located in the conserved env region among the oncoretroviruses.

An amplification product of 1932 by was obtained and cloned in the following manner:

the amplified DNA was inserted into a plasmid with the aid of the TA Cloning Kit®. The various steps were carried out in accordance with the instructions for the TA Cloning Kit® (Invitrogen). At the end of the procedure, the white colonies of recombinant bacteria (white) were subcultured so as to be cultured and allow the extraction of the plasmids incorporated according to the so-called "miniprep" procedure. The plasmid preparation of each recombinant colony was cut with an appropriate restriction enzyme and analyzed on agarose gel. The plasmids possessing an insert detected under UV light after staining the gel with ethidium bromide were selected for the sequencing of the insert after hybridization with a primer complementary to the SP6 promoter present on the cloning plasmid of the TA cloning Kit®. The reaction prior to the sequencing was then carried out according to the method recommended for using the sequencing kit "PRISM™ Ready Reaction AmpliTaq® FS, DyeDeoxy™ Terminator" (Applied Biosystems, ref. 402119) and the automated sequencing was carried out on the Applied Biosystems 373 A and 377 apparatus, according to the manufacturer's instructions.

The C15 clone obtained contains a region corresponding to the region of the MSRV-1 envelope of 1481 bp.

The env region of the C15 clone is represented by its nucleotide sequence (SEQ ID NO: 9) in FIG. 4. The three potential reading frames of this clone are presented by their amino acid sequence under the nucleotide sequence. The reading frame corresponding to an MSRV-1 structural env protein is identified by SEQ ID NO: 10.

From the defined sequences obtained from clones c16 and C15, it was possible to produce a plasmid construct encoding a complete envelope followed by the 3' LTR, as presented in FIG. 13 with the corresponding reading frame.

Example 3

Preparation of a 5M6 Clone Containing the Sequences of the 3' Terminal Region of the Envelope, Followed by the MSRV-1 Proviral Type U3, R and U5 Sequences A monodirectional PCR was carried out on the DNA extracted from immortalized B lymphocytes in culture from an MS patient. The PCR was carried out with Expand™ Long Template PCR System (Boehringer) under the following conditions: 94° C. 3 min then 93° C. 1 min, 60° C. 1 min, 68° C. 3 min over 10 cycles, then 93° C. 1 min, 60° C. 1 min with 15 sec of extension at each cycle, 68° C. 3 min over 35 cycles and 68° C. for 7 min and with a final reaction volume of 50 µl.

The primer used for the PCR identified by SEQ ID NO: 11 is 5' TCA AAA TCG AAG AGC TTT AGA CTT GCT AAC CG 3'.

The primer of SEQ ID NO: 11 is specific for the env region of the C15 clone.

An amplification product of 1673 by was obtained and cloned in the following manner:

the amplified DNA was inserted into a plasmid with the aid of the TA Cloning Kit®. The various steps were carried out in accordance with the instructions for the TA Cloning Kit® (Invitrogen). At the end of the procedure, the white colonies of recombinant bacteria (white) were subcultured so as to be cultured and allow the extraction of the plasmids incorporated according to the so-called "miniprep" procedure. The plasmid preparation of each recombinant colony was cut with an appropriate restriction enzyme and analyzed on agarose gel. The plasmids possessing an insert detected under UV light after staining the gel with ethidium bromide were selected for the sequencing of the insert after hybridization with a primer complementary to the T7 promoter present on the cloning plasmid of the TA cloning Kit©. The reaction prior to the sequencing was then carried out according to the method recommended for using the sequencing kit "PRISM™ Ready Reaction AmpliTaq° FS, DyeDeoxy™ Terminator" (Applied Biosystems, ref. 402119) and the automated sequencing was carried out on the Applied Biosystems 373 A and 377 apparatus, according to the manufacturer's instructions.

The 5M6 clone obtained contains a region corresponding to the 3' region of the MSRV-1 envelope of 492 by followed by the regions U3, R and U5 (837 bp) of MSRV1.

The 5M6 clone is represented by its nucleotide sequence (SEQ ID NO: 12) in FIG. 5. The three potential reading frames of this clone are presented by their amino acid sequence under the nucleotide sequence. The reading frame corresponding to the C-terminal end of the MSRV-1 env protein is identified by SEQ ID NO: 13.

Example 4

Preparation of the LB16 Clone Containing the Region Encoding the MSRV-1 Retrovirus Integrase An RT-PCR was carried out on the total RNA treated with DNAseI and extracted from a choroid plexus obtained from an MS patient. The synthesis of cDNA was carried out with an oligo dT primer and the reverse transcriptase "Expand™ RT" from Boehringer according to the conditions recommended by the company. A "no RT" control was carried out in parallel on the same material. A PCR was carried out with Taq polymerase (Perkin Elmer) under the following conditions: 95° C. 5 min, then 95° C. 1 min, 55° C. 1 min, 72° C. 2 min over 35 cycles and 72° C. for 8 min and with a final reaction volume of 50

Primers used for the PCR:

```
5' primer, identified by SEQ ID NO: 14

5' GGC ATT GAT AGC ACC CAT CAG 3';

3' primer, identified by SEQ ID NO: 15

5' CAT GTC ACC AGG GTG GAA TAG 3'
```

The primer SEQ ID NO: 14 is specific for the pol region of MSRV-1 and more precisely similar to the integrase region described above. The primer SEQ ID NO: 15 was defined on sequences of the clones obtained during preliminary tests.

An amplification product of about 760 by was obtained only in the test with RT and was cloned in the following manner:

the amplified DNA was inserted into a plasmid with the aid of the TA Cloning Kit®. The various steps were carried out in accordance with the instructions for the TA Cloning Kit® (Invitrogen). At the end of the procedure, the white colonies of recombinant bacteria (white) were subcultured so as to be cultured and allow the extraction of the plasmids incorporated according to the so-called "miniprep" procedure. The plasmid preparation of each recombinant colony was cut with an appropriate restriction enzyme and analyzed on agarose gel. The plasmids possessing an insert detected under UV light after staining the gel with ethidium bromide were selected for the sequencing of the insert after hybridization with a primer complementary to the T7 promoter present on the cloning plasmid of the TA cloning Kit®. The reaction prior to the sequencing was then carried out according to the method recommended for using the sequencing kit "PRISM™ Ready Reaction AmpliTaq® FS, DyeDeoxy™ Terminator" (Applied Biosystems, ref. 402119) and the automated sequencing was carried out on the Applied Biosystems 373 A and 377 apparatus, according to the manufacturer's instructions.

The LB16 clone obtained contains the sequences corresponding to integrase. The nucleotide sequence of this clone was identified by SEQ ID NO: 16 in FIG. 11, three reading frames are determined.

Example 5

Preparation of a Clone 2, CL2, Containing in 3' a Portion Homologous to the POL Gene, Corresponding to the Protease Gene, and to the Gag Gene (GM3) Corresponding to the Nucleocapsid, and a New 5'Coding Region, Corresponding to the Gag Gene More Specifically the Template and the Capsid of MSRV-1

A PCR amplification was carried out on the total RNA extracted from 100 µl of plasma from a patient suffering from MS. A water control, treated under the same conditions, was used as negative control. The synthesis of cDNA was carried out with 300 pmol of a random primer (GIBCO-BRL, France) and the reverse transcriptase "Expand RT" (BOEHRINGER MANNHEIM, France) according to the conditions recommended by the company. An amplification by PCR ("polymerase chain reaction") was carried out with the enzyme Taq polymerase (Perkin Elmer, France) using 10 µl of cDNA under the following conditions: 94° C. 2 min, 55° C. 1 min, 72° C. 2 min then 94° C. 1 min, 55° C. 1 min, 72° C. 2 min over 30 cycles and 72° C. for 7 min with a final reaction volume of 50 µl.

Primers used for the PCR amplification:

```
5' primer, identified by SEQ ID NO: 17

5' CGG ACA TCC AAA GTG ATG GGA AAC G 3';

3' primer, identified by SEQ ID NO: 18

5' GGA CAG GAA AGT AAG ACT GAG AAG GC 3'
```

A second amplification by so-called "seminested" PCR was carried out with a 5' primer situated inside the region already amplified. This second PCR was carried out under the same experimental conditions as those used during the first PCR, using 10 µl of the amplification product derived from the first PCR.

Primers used for the amplification by seminested PCR:

```
5' primer, identified by SEQ ID NO: 19

5' CCT AGA ACG TAT TCT GGA GAA TTG GG 3';

3' primer, identified by SEQ ID NO: 20

5' TGG CTC TCA ATG GTC AAA CAT ACC CG 3'
```

The primers SEQ ID NO: 18 and SEQ ID NO: 20 are specific for the pol region, clone G+E+A, more specifically the E region: nucleotide position No. 423 to No. 448. The primers used in the 5' region were defined on sequences of clones obtained during preliminary tests.

An amplification product of 1511 by was obtained from the RNA extracted from the plasma of an MS patient. The corresponding fragment was not observed for the water control. This amplification product was cloned in the following manner.

The amplified DNA was inserted into a plasmid with the aid of the TA Cloning Kit™. The 2 µl of DNA solution were mixed with 5-11 of sterile distilled water, 1 µl of a 10 times concentrated ligation buffer "10× LIGATION BUFFER", 2 µl of "pCR™ VECTOR" (25 ng/ml) and 1 µl of "T4 DNA LIGASE". This mixture was incubated overnight at 14° C. The following steps were carried out in accordance with the instructions of the TA Cloning Kit® (Invitrogen). The mixture was plated after transformation of the ligation into *E. coli* INVαF' bacteria. At the end of the procedure, the white colonies of recombinant bacteria were subcultured so as to be cultured and allow the extraction of the plasmids incorporated according to the so-called "DNA minipreparation" procedure (17). The plasmid preparation of each recombinant colony was cut with the restriction enzyme EcoRI and analyzed on agarose gel. The plasmids possessing an insert detected under UV light after staining the gel with ethidium bromide were selected for the sequencing of the insert after hybridization with a primer domplementary to the T7 promoter present on the cloning plasmid of the TA cloning Kit®. The reaction prior to the sequencing was then carried out according to the method recommended for using the sequencing kit "PRISM™ Ready Reaction Amplitaq® FS, DyeDeoxy™ Terminator" (Applied Biosystems, ref. 402119) and the automated sequencing was carried out on the Applied Biosystems 373 A and 377 apparatus, according to the manufacturer's instructions.

The clone obtained, called CL2, contains a C-terminal region similar to the 5' terminal region of the clones G+E+A of MSRV-1, which makes it possible to define the C-terminal region of the gag gene and a new region corresponding to the N-terminal region of the MSRV-1 gag gene.

CL2 makes it possible to define a region of 1511 by having an open reading frame in the N-terminal region of 1077 by encoding 359 amino acids and a non-open reading frame of 454 by corresponding to the C-terminal region of the MSRV-1 gag gene.

The nucleotide sequence of CL2 is identified by SEQ ID NO: 21. It is represented in FIG. 6 with the potential reading frames in amino acids.

The 1077 by fragment of CL2 encoding 359 amino acids was amplified by PCR with the Pwo enzyme (5 U/µl) (Boehringer Mannheim, France) using 1 µl of the DNA minipreparation of clone 2 under the following conditions: 95° C. 1 min, 60° C. 1 min, 72° C. 2 min over 25 cycles and with a final reaction volume of 50 µl with the aid of the primers:

```
5' primer (BamHI), identified by SEQ ID NO: 23

5' TGC TGG AAT TCG GGA TCC TAG AAC GTA TTC 3'
(30 mer), and

3' primer (HindIII), identified by SEQ ID NO: 24

5' AGT TCT GCT CCG AAG CTT AGG CAG ACT TTT 3'

(30 mer) corresponding, respectively, to the
nucleotide sequence of clone 2 at position -9 to 21
and 1066 to 1095.
```

The fragment obtained by PCR was linearized with BamHI and HindIII and subcloned into the expression vectors pET28C and pET21C (NOVAGEN) linearized with BamHI and HindIII. The sequencing of the DNA of the 1077 by fragment of clone 2 in the two expression vectors was carried out according to the method recommended for the use of the sequencing kit "PRISM™ Ready Reaction Amplitaqe® FS, DyeDeoxy™ Terminator" (Applied Biosystems, ref. 402119 and the automated sequencing was carried out on the Applied Biosystems 373 A and 377 apparatus, according to the manufacturer's instructions.

The expression of the nucleotide sequence of the 1077 by fragment of clone 2 by the expression vectors pET28C and pET21C are identified by SEQ ID NO: 25 and SEQ ID NO: 26, respectively.

Example 6

Expression of Clone 2 in *Escherichia coli*

The constructs pET28c-clone 2 (1077 bp) and pET21C-clone 2 (1077 bp) synthesize, in the bacterial strain BL21 (DE3), a protein fused at the N- and C-terminus for the vector pET28C and the C-terminus for the vector pET21C with 6 Histidines, having an apparent molecular mass of about 45 kDa, identified by SDS-PAGE polyacrylamide gel electrophoresis (SDS=Sodium Dodecyl Sulfate) (Laemmli, 1970 (1)). The reactivity of the protein was demonstrated towards an anti-Histidine monoclonal antibody (DIANOVA) by the Western-blot technique (Towbin et al., 1979 (2)).

The recombinant proteins pET28c-clone 2 (1077 bp) and pET21C-clone 2 (1077 bp) were visualized by SDS-PAGE in the insoluble fraction after enzymatic digestion of the bacterial extracts with 50 gl of lysozyme (10 mg/ml) and ultrasound lysis.

The antigenic properties of the recombinant antigens pET28C-clone 2 (1077 bp) and pET21C-clone 2 (1077 bp)

were tested by Western blot after solubilization of the bacterial pellet with 2% SDS and 50 mM β-mercaptoethanol. After incubation with sera from patients suffering from multiple sclerosis, the sera from neurological controls and the sera from controls at the Blood Transfusion Center (CTS), the immunocomplexes were detected with the aid of an alkaline phosphatase-coupled goat serum anti-human IgG and anti-human IgM.

The results are presented in the table below.

TABLE

Reactivity of sera affected by multiple sclerosis and controls with the MSRV-1 recombinant protein gag clone 2 (1077 bp) = pET21C-clone 2 (1077 bp) and pET28C-clone 2 (1077 bp)[a]

| DISEASE | NUMBER OF INDIVIDUALS TESTED | NUMBER OF POSITIVE INDIVIDUALS |
| --- | --- | --- |
| MS | 15 | 6 |
|  |  | 2 (+++), 2 (++), 2 (+) |
| NEUROLOGICAL CONTROLS | 2 | 1 (+++) |
| HEALTHY CONTROLS (CTS) | 22 | 1 (+/−) |

[a]The strips containing 1.5 µg of recombinant antigen pET-gag clone 2 (1077 bp) exhibit reactivity against sera diluted 1/100. The Western-Blot interpretation is based on the presence or absence of a specific pET-gag clone 2 (1077 bp) band on the strips. Positive and negative controls are included in each experiment.

These results show that, under the technical conditions used, about 40% of the human sera affected by multiple sclerosis which were tested react with the recombinant proteins pET28C-clone 2 (1077 bp) and pET21C-clone 2 (1077 bp). Reactivity was observed on a neurological control and it is of interest to note that the RNAs extracted from this serum, after the reverse transcriptase step, are also amplified by PCR in the pol region. This suggests that people who have not declared MS may also harbor and express this virus. On the other hand, an apparently healthy control (CTS donor) possesses anti-gag (clone 2, 1077 bp) antibodies. This is compatible with an immunity acquired against MSRV-1 independently of a declared associated autoimmune disease.

Example 7

Preparation of an LB13 Clone Containing in 3' a Portion Homologous to Clone 2 Corresponding to the Gag Gene and in 5' a Portion Homologous to the 5M6 Clone Corresponding to the U5 LTR Region An RT-PCR ("reverse transcriptase-polymerase chain reaction") was carried out using total RNA extracted from virions, obtained from supernatants of B lymphocyte cells of patients suffering from multiple sclerosis, concentrated by ultracentrifugations. The synthesis of cDNA was carried out with a specific primer SEQ ID NO: 27 and the reverse transcriptase "Expand™ RT" from BOEHRINGER MANNHEIM according to the conditions recommended by the company.

Primer used for the synthesis of the cDNA, identified by SEQ ID NO: 27:

5' CTT GGA GGG TGC ATA ACC AGG GAA T 3'

A PCR amplification was carried out with Taq polymerase (Perkin Elmer, France) under the following conditions: 94° C. 1 min, 55° C. 1 min, 72° C. 2 min over 35 cycles at 72° C. for 7 min and with a final reaction volume of 100

Primers used for the PCR amplification:

5' primer, identified by SEQ ID NO: 28

5' TGT CCG CTG TGC TCC TGA TC 3'

3' primer, identified by SEQ ID NO: 27

5' CTT GGA GGG TGC ATA ACC AGG GAA T 3'

A second so-called "seminested" PCR amplification was carried out with a 3' primer situated inside the region already amplified. This second amplification was carried out under the same experimental conditions as those used during the first amplification, using 10 µl of the amplification product derived from the first PCR.

Primers used for the "seminested" PCR amplification:

5' primer, identified by SEQ ID NO: 28

5' TGT CCG CTG TGC TCC TGA TC 3'

3' primer, identified by SEQ ID NO: 29

5' CTA TGT CCT TTT GGA CTG TTT GGG T 3'

The primers SEQ ID NO: 27 and SEQ ID NO: 29 are specific for the gag region, clone 2 nucleotide position No. 373-397 and No. 433-456. The primers used in the 5' region were defined on sequences of the clones obtained during preliminary tests.

An amplification product of 764 by was obtained and cloned in the following manner:

The amplified DNA was inserted into a plasmid with the aid of the TA Cloning Kit™. The 2 µl of DNA solution were mixed with 5 µl of sterile distilled water, 1 µl of a 10 times concentrated ligation buffer "10× LIGATION BUFFER", 2 µl of "pCR™ VECTOR" (25 ng/ml) and 1 µl of "T4 DNA LIGASE". This mixture was incubated overnight at 14° C. The following steps were carried out in accordance with the instructions of the TA Cloning Kit® (Invitrogen). The mixture was plated after transformation of the ligation into E. coli INVαF' bacteria. At the end of the procedure, the white colonies of recombinant bacteria were subcultured so as to be cultured and allow the extraction of the plasmids incorporated according to the so-called "DNA minipreparation" procedure (17). The plasmid preparation of each recombinant colony was cut with the restriction enzyme EcoRI and analyzed on agarose gel. The plasmids possessing an insert detected under UV light after staining the gel with ethidium bromide were selected for the sequencing of the insert after hybridization with a primer complementary to the T7 promoter present on the cloning plasmid of the TA cloning Kit®. The reaction prior to the sequencing was then carried out according to the method recommended for using the sequencing kit "PRISM™ Ready Reaction Amplitaq® FS, DyeDeoxy™ Terminator" (Applied Biosystems, ref. 402119) and the automated sequencing was carried out on the Applied Biosystems 373 A and 377 apparatus, according to the manufacturer's instructions.

The LB13 clone obtained contains an N-terminal region of MSRV-1 gag gene homologous to clone 2 and an LTR corresponding to a portion of the U5 region. Between the U5 region and gag, a binding site for the transfer RNAs, the PBS "primer binding site", was identified.

The nucleotide sequence of the 764 by fragment of the LB13 clone in the plasmid "pCR™ vector" is represented in the identifier SEQ ID NO: 30.

The binding site for the transfer RNAs, having a sequence of PBS tryptophan type, was identified at nucleotide position No. 342-359 of the LB13 clone.

As this same PBS was found in the endogenous copies homologous to MSRV1, the endogenous family thus defined is henceforth called HERV W, according to the nomenclature proposed for the endogenous retrovirus families (W=tryptophan).

A short ORF of about 65 amino acids was found in the U5 region of the 5' LTR of the LB13 clone.

```
Sequence of the ORF (SEQ ID NO: 32):
PMASNRAITLTAWSKIPFLGIRETKNPRSENTRLATMLEAAHHHFGSSPPL

SWELWEQGPQVTIW.
```

The corresponding nucleotide sequence starting at an ATG codon is capable of being expressed in a subgenomic DNA from a proviral LTR (U3RU5).

Another clone, called LA15, was obtained on the total RNA extracted from virions concentrated by ultracentrifugation from a culture supernatant of synoviocytes obtained from a patient suffering from rheumatoid arthritis. The strategy for amplifying and cloning the LA15 clone is exactly the same which was used for the LB13 clone.

The nucleotide sequence of the LA15 clone, which is represented in the identifier SEQ ID NO: 31, is very similar to the LD13 clone. This suggests that the MSVR-1 retrovirus detected in multiple sclerosis has sequences which are similar to those found in rheumatoid arthritis.

Example 8

Reconstruction of an RU5-GAG Region from the Clones LB15, LB13, CL2 and CL17

The clones CL2 and LB13 have already been described in the preceding examples. The LB15 clone was obtained using the R sequence of the LTR of the c16 clone in order to define a primer in 5' and the antisense primers used are the same as for the LB13 clone. The CL17 clone was obtained by nested RT-PCR using the following primers:

```
                                           (SEQ ID NO: 33)
5'-TCATGCAACTGCACTCTTCTGGTCCG-3' (sense)

(SEQ ID NO: 34)
5'-TCTTGCACTAACCTCCACTGTCCGTTGG-3' (antisense)

(SEQ ID NO: 35)
5'-ATCCCCCAGTAACAATTTGGTGACCACG-3' (sense)

(SEQ ID NO: 36)
5'-TCGGGTCTAAGAGGGTACTTCCTTTGGTAGG-3' (antisense)
```

The LB15 clone was obtained from virions obtained by culturing MS cells. The LB17 clone was obtained from culturing plasma from an MS patient.

These overlapping clones made it possible to reconstruct an RU5-gag sequence with a potential ORF in the gag gene, as presented in FIG. 14.

Example 9

Preparation of a Clone 87-23

The region corresponding to integrase was amplified and cloned from MS plasma using a seminested RT PCR with the following primers situated in the pol and env regions of MSRV1.

In the pol region:

```
                                           (SEQ ID NO: 37)
5'-TTACGCAGGTCTCAGGGATGAGCTT-3' (sense-primary PCR)

(SEQ ID NO: 38)
5'-CGGCAGTAGCAGTCTTAGTATCTGAAGCAGTTA-3'
(sense-secondary PCR)
```

In the env region,

```
5'-GGTACGGAGGGTTTCATGTAGTTTTGAG-3' (SEQ ID NO: 39)
(anti-sense primary and secondary PCR)
```

The amplified clone contains 774 by in the pol/RT region, all the integrase region (1197 bp) and the start of the env region (480 bp). The nucleotide sequence corresponding to the integrase region and the translation to amino acids of the potential ORF are presented in FIG. 15.

Example 10

Confirmation of the Presence of RNA Containing Env Sequences Related to ERV9 in the Retroviral Particles Associated with the MSRV1 Genome Sequences related to ERV9 have been found in a minor proportion in the virion preparations obtained from MS compared with the MSRV1 sequences. The existence of phenomena of co-encapsidation of phylogenetically related endogenous sequences into retroviral particles produced by a replicative strain has been described. Surprisingly, an RNA region comprising an ORF starting in the 3' portion of env and continuing potentially into the 3' LTR has been found in various MS samples. In order to specify the existence of an ORF, transcription-translation tests were carried out and made it possible to show the reality of an env ORF containing the entire transmembrane (TM) portion and ending at the start of the putative LTR. However, an additional frame (ORFX) follows and continues in the 3' LTR. The two products of expression were visualized and their respective ORFs were subcloned. FIG. 16 represents the nucleotide and peptide sequences of the B13 clone already described, specifying the ORFs in the truncated env region and in the putative LTR. The presence of such RNAs may be responsible for recombinations with the replicative strain and consequently generate strains having a modified pathogenicity.

BIBLIOGRAPHIC REFERENCES (1) Laemmli U. K. Cleavage of structural proteins during the assembly of the head of bacteriophage T4. Nature. (1970). 227: 680-685.

(2) Towbin H., Staehelin T. & Gordon J. Electrophoretic transfer of proteins from polyacrylamide gels to nitrocellulose sheets: procedure and some applications. Proc. Natl. Acad. Sci. USA. (1979). 76: 4350-4354.

SEQUENCE LISTING

<160> NUMBER OF SEQ ID NOS: 45

<210> SEQ ID NO 1
<211> LENGTH: 34
<212> TYPE: DNA
<213> ORGANISM: MSRV

<400> SEQUENCE: 1
gactcgctgc agatcgattt ttttttttt tttt                                    34

<210> SEQ ID NO 2
<211> LENGTH: 30
<212> TYPE: DNA
<213> ORGANISM: MSRV

<400> SEQUENCE: 2
gccatcaagc cacccaagaa ctcttaactt                                        30

<210> SEQ ID NO 3
<211> LENGTH: 30
<212> TYPE: DNA
<213> ORGANISM: MSRV

<400> SEQUENCE: 3
ccaatagcca gaccattata tacactaatt                                        30

<210> SEQ ID NO 4
<211> LENGTH: 310
<212> TYPE: DNA
<213> ORGANISM: MSRV

<400> SEQUENCE: 4
gcttatagaa ggacccctag tatggggtaa tccctctgg gaaaccaagc cccagtactc         60
agcaggaaaa atagaatagg aaacctcaca aggacatact ttcctcccct ccagatggct       120
agccactgag gaaggaaaaa tactttcacc tgcagctaac caacagaaat tacttaaaac       180
ccttcaccaa accttccact taggcattga tagcacccat cagatggcca aattattatt       240
tactggacca ggccttttca aaactatcaa gaagatagtc aggggctgtg aagtgtgcca       300
aagaaataat                                                             310

<210> SEQ ID NO 5
<211> LENGTH: 103
<212> TYPE: PRT
<213> ORGANISM: MSRV
<220> FEATURE:
<221> NAME/KEY: misc_feature
<222> LOCATION: (26)..(26)
<223> OTHER INFORMATION: Xaa = any amino acid

<400> SEQUENCE: 5

Leu Ile Glu Gly Pro Leu Val Trp Gly Asn Pro Leu Trp Glu Thr Lys
1               5                   10                  15

Pro Gln Tyr Ser Ala Gly Lys Ile Glu Xaa Glu Thr Ser Gln Gly His
            20                  25                  30

Thr Phe Leu Pro Ser Arg Trp Leu Ala Thr Glu Glu Gly Lys Ile Leu
        35                  40                  45

Ser Pro Ala Ala Asn Gln Gln Lys Leu Leu Lys Thr Leu His Gln Thr
    50                  55                  60

Phe His Leu Gly Ile Asp Ser Thr His Gln Met Ala Lys Leu Leu Phe 65                  70                  75                  80
Thr Gly Pro Gly Leu Phe Lys Thr Ile Lys Lys Ile Val Arg Gly Cys
                85                  90                  95
Glu Val Cys Gln Arg Asn Asn
            100

<210> SEQ ID NO 6
<211> LENGTH: 635
<212> TYPE: DNA
<213> ORGANISM: MSRV

<400> SEQUENCE: 6
ccctgtatct ttaacctcct tgttaagttt gtctcttcca gaatcaaaac tgtaaaacta    60
caaattgttc ttcaaatgga gcaccagatg gagtccatga ctaagatcca ccgtggaccc   120
ctggaccggc ctgctagccc atgctccgat gttaatgaca ttgaaggcac ccctcccgag   180
gaaatctcaa ctgcacaacc cctactatgc cccaattcag cgggaagcag ttagagcggt   240
catcagccaa cctccccaac agcacttggg ttttcctgtt gagagggggg actgagagac   300
aggactagct ggatttccta ggccaacgaa gaatccctaa gcctagctgg aaggtgact    360 gcatccacct ctaaacatgg gcttgcaac ttagctcaca cccgaccaat cagagagctc     420
actaaaatgc taattaggca aaataggag gtaaagaaat agccaatcat ctattgcctg     480
agagcacagc gggagggaca aggatcggga tataaaccca ggcattcgag ccggcaacgg   540 caacccctt tgggtcccct cctttgtat gggcgctctg ttttcactct atttcactct      600
attaaatctt gcaactgaaa aaaaaaaaaa aaaaa                                635

<210> SEQ ID NO 7
<211> LENGTH: 77
<212> TYPE: PRT
<213> ORGANISM: MSRV

<400> SEQUENCE: 7

Pro Cys Ile Phe Asn Leu Leu Val Lys Phe Val Ser Ser Arg Ile Lys
1               5                   10                  15

Thr Val Lys Leu Gln Ile Val Leu Gln Met Glu His Gln Met Glu Ser
            20                  25                  30

Met Thr Lys Ile His Arg Gly Pro Leu Asp Arg Pro Ala Ser Pro Cys
            35                  40                  45

Ser Asp Val Asn Asp Ile Glu Gly Thr Pro Pro Glu Glu Ile Ser Thr
        50                  55                  60

Ala Gln Pro Leu Leu Cys Pro Asn Ser Ala Gly Ser Ser
65                  70                  75

<210> SEQ ID NO 8
<211> LENGTH: 32
<212> TYPE: DNA
<213> ORGANISM: MSRV

<400> SEQUENCE: 8
tggggttcca tttgtaagac catctgtagc tt                                   32

<210> SEQ ID NO 9
<211> LENGTH: 1481
<212> TYPE: DNA
<213> ORGANISM: MSRV

<400> SEQUENCE: 9

-continued

```
atggccctcc cttatcatac ttttctcttt actgttctct taccccccttt cgctctcact     60 gcaccccctc catgctgctg tacaaccagt agctccccctt accaagagtt tctatgaaga    120
acgcggcttc ctggaaatat tgatgcccca tcatatagga gtttatctaa gggaaactcc    180
accttcactg cccacaccca tatgccccgc aactgctata actctgccac tctttgcatg    240
catgcaaata ctcattattg gacagggaaa atgattaatc ctagttgtcc tggaggactt    300
ggagccactg tctgttggac ttacttcacc cataccagta tgtctgatgg gggtggaatt    360
caaggtcagg caagagaaaa acaagtaaag gaagcaatct cccaactgac ccggggacat    420
agcaccccta gcccctacaa aggactagtt ctctcaaaac tacatgaaac cctccgtacc    480
catactcgcc tggtgagcct atttaatacc accctcactc ggctccatga ggtctcagcc    540
caaaacccta ctaactgttg gatgtgcctc cccctgcact tcaggccata catttcaatc    600
cctgttcctg aacaatggaa caacttcagc acagaaataa acaccacttc cgttttagta    660
ggacctcttg tttccaatct ggaaataacc catacctcaa acctcacctg tgtaaaattt    720
agcaatacta tagacacaac cagctcccaa tgcatcaggt gggtaacacc tcccacacga    780
atagtctgcc taccctcagg aatatttttt gtctgtggta cctcagccta tcattgtttg    840
aatggctctt cagaatctat gtgcttcctc tcattcttag tgccccctat gaccatctac    900
actgaacaag atttatacaa tcatgtcgta cctaagcccc acaacaaaag agtacccatt    960
cttccttttg ttatcagagc aggagtgcta ggcagactag gtactggcat tggcagtatc   1020
acaacctcta ctcagttcta ctacaaacta tctcaagaaa taaatggtga catggaacag   1080
gtcactgact ccctggtcac cttgcaagat caacttaact ccctagcagc agtagtcctt   1140
caaaatcgaa gagctttaga cttgctaacc gccaaaagag ggggaacctg tttatttttta   1200 ggagaagaac gctgttatta tgttaatcaa tccagaattg tcactgagaa agttaaagaa   1260
attcgagatc gaatacaatg tagagcagag gagcttcaaa acaccgaacg ctggggcctc   1320
ctcagccaat ggatgccctg ggttctcccc ttcttaggac ctctagcagc tctaatattg   1380
ttactcctct ttggaccctg tatctttaac ctccttgtta agtttgtctc ttccagaatt   1440
gaagctgtaa agctacagat ggtcttacaa atggaacccc a                        1481
```

```

<210> SEQ ID NO 10
<211> LENGTH: 493
<212> TYPE: PRT
<213> ORGANISM: MSRV
<220> FEATURE:
<221> NAME/KEY: misc_feature
<222> LOCATION: (39)..(39)
<223> OTHER INFORMATION: Xaa = any amino acid

<400> SEQUENCE: 10

Met Ala Leu Pro Tyr His Thr Phe Leu Phe Thr Val Leu Leu Pro Pro
1               5                   10                  15

Phe Ala Leu Thr Ala Pro Pro Pro Cys Cys Cys Thr Thr Ser Ser Ser
            20                  25                  30

Pro Tyr Gln Glu Phe Leu Xaa Arg Thr Arg Leu Pro Gly Asn Ile Asp
        35                  40                  45

Ala Pro Ser Tyr Arg Ser Leu Ser Lys Gly Asn Ser Thr Phe Thr Ala
    50                  55                  60

His Thr His Met Pro Arg Asn Cys Tyr Asn Ser Ala Thr Leu Cys Met
65                  70                  75                  80

His Ala Asn Thr His Tyr Trp Thr Gly Lys Met Ile Asn Pro Ser Cys
                85                  90                  95
```

```
Pro Gly Gly Leu Gly Ala Thr Val Cys Trp Thr Tyr Phe Thr His Thr
            100                 105                 110

Ser Met Ser Asp Gly Gly Ile Gln Gly Gln Ala Arg Glu Lys Gln
        115                 120                 125

Val Lys Glu Ala Ile Ser Gln Leu Thr Arg Gly His Ser Thr Pro Ser
    130                 135                 140

Pro Tyr Lys Gly Leu Val Leu Ser Lys Leu His Glu Thr Leu Arg Thr
145                 150                 155                 160

His Thr Arg Leu Val Ser Leu Phe Asn Thr Thr Leu Thr Arg Leu His
                165                 170                 175

Glu Val Ser Ala Gln Asn Pro Thr Asn Cys Trp Met Cys Leu Pro Leu
            180                 185                 190

His Phe Arg Pro Tyr Ile Ser Ile Pro Val Pro Glu Gln Trp Asn Asn
                195                 200                 205

Phe Ser Thr Glu Ile Asn Thr Thr Ser Val Leu Val Gly Pro Leu Val
        210                 215                 220

Ser Asn Leu Glu Ile Thr His Thr Ser Asn Leu Thr Cys Val Lys Phe
225                 230                 235                 240

Ser Asn Thr Ile Asp Thr Thr Ser Ser Gln Cys Ile Arg Trp Val Thr
                245                 250                 255

Pro Pro Thr Arg Ile Val Cys Leu Pro Ser Gly Ile Phe Phe Val Cys
            260                 265                 270

Gly Thr Ser Ala Tyr His Cys Leu Asn Gly Ser Ser Glu Ser Met Cys
        275                 280                 285

Phe Leu Ser Phe Leu Val Pro Pro Met Thr Ile Tyr Thr Glu Gln Asp
    290                 295                 300

Leu Tyr Asn His Val Val Pro Lys Pro His Asn Lys Arg Val Pro Ile
305                 310                 315                 320

Leu Pro Phe Val Ile Arg Ala Gly Val Leu Gly Arg Leu Gly Thr Gly
                325                 330                 335

Ile Gly Ser Ile Thr Thr Ser Thr Gln Phe Tyr Tyr Lys Leu Ser Gln
            340                 345                 350

Glu Ile Asn Gly Asp Met Glu Gln Val Thr Asp Ser Leu Val Thr Leu
        355                 360                 365

Gln Asp Gln Leu Asn Ser Leu Ala Ala Val Val Leu Gln Asn Arg Arg
    370                 375                 380

Ala Leu Asp Leu Leu Thr Ala Lys Arg Gly Gly Thr Cys Leu Phe Leu
385                 390                 395                 400

Gly Glu Glu Arg Cys Tyr Tyr Val Asn Gln Ser Arg Ile Val Thr Glu
                405                 410                 415

Lys Val Lys Glu Ile Arg Asp Arg Ile Gln Cys Arg Ala Glu Glu Leu
            420                 425                 430

Gln Asn Thr Glu Arg Trp Gly Leu Leu Ser Gln Trp Met Pro Trp Val
        435                 440                 445

Leu Pro Phe Leu Gly Pro Leu Ala Ala Leu Ile Leu Leu Leu Leu Phe
    450                 455                 460

Gly Pro Cys Ile Phe Asn Leu Leu Val Lys Phe Val Ser Ser Arg Ile
465                 470                 475                 480

Glu Ala Val Lys Leu Gln Met Val Leu Gln Met Glu Pro
                485                 490

<210> SEQ ID NO 11
<211> LENGTH: 32
```

```
<212> TYPE: DNA
<213> ORGANISM: MSRV

<400> SEQUENCE: 11
tcaaaatcga agagctttag acttgctaac cg                                     32

<210> SEQ ID NO 12
<211> LENGTH: 1329
<212> TYPE: DNA
<213> ORGANISM: MSRV
<220> FEATURE:
<221> NAME/KEY: misc_feature
<222> LOCATION: (594)..(594)
<223> OTHER INFORMATION: n = a, g, c or t/u
<220> FEATURE:
<221> NAME/KEY: misc_feature
<222> LOCATION: (602)..(602)
<223> OTHER INFORMATION: n = a, g, c or t/u
<220> FEATURE:
<221> NAME/KEY: misc_feature
<222> LOCATION: (1232)..(1232)
<223> OTHER INFORMATION: n = a, g, c or t/u

<400> SEQUENCE: 12
tcaaaatcga agagctttag acttgctaac cgccaaaaga gggggaacct gtttattttt      60
aggggaagaa tgctgttagt atgttaatca atctggaatc attactgaga aagttaaaga    120
aatttgagat cgaatataat gtagagcaga ggaccttcaa acactgcac cctggggcct     180 cctcagccaa tggatgccct ggactctccc cttcttagga cctctagcag ctataatatt    240
tttactcctc tttggaccct gtatcttcaa cttccttgtt aagtttgtct cttccagaat    300
tgaagctgta aagctacaaa tagttcttca aatggaaccc cagatgcagt ccatgactaa    360
aatctaccgt ggaccctgg accggcctgc tagactatgc tctgatgtta atgacattga    420
agtcacccct cccgaggaaa tctcaactgc acaacccta ctacactcca attcagtagg     480
aagcagttag agcagttgtc agccaacctc cccaacagta cttgggtttt cctgttgaga    540
gggtggactg agagacagga ctagctggat ttcctaggct gactaagaat cccnaagcct    600
anctgggaag gtgaccgcat ccatctttaa acatgggggct tgcaacttag ctcacacccg    660
accaatcaga gagctcacta aaatgctaat caggcaaaaa caggaggtaa agcaatagcc    720
aatcatctat tgcctgagag cacagcggga aggacaagga ttgggatata aactcaggca    780
ttcaagccag caacagcaac ccccttggg tcccctccca ttgtatggga gctctgtttt     840
cactctattt cactctatta aatcatgcaa ctgcactctt ctggtccgtg ttttttatgg    900
ctcaagctga gcttttgttc gccatccacc actgctgttt gccaccgtca cagacccgct    960
gctgacttcc atcccttttgg atccagcaga gtgtccactg tgctcctgat ccagcgaggt   1020
acccattgcc actcccgatc aggctaaagg cttgccattg ttcctgcatg gctaagtgcc    1080
tgggtttgtc ctaatagaac tgaacactgg tcactgggtt ccatggttct cttccatgac    1140
ccacggcttc taatagagct ataacactca ccgcatggcc caagattcca ttccttggta    1200
tctgtgaggc caagaacccc aggtcagaga angtgaggct tgccaccatt tgggaagtgg    1260
cccactgcca ttttggtagc ggcccaccac catcttggga gctgtgggag caaggatccc    1320
ccagtaaca                                                           1329

<210> SEQ ID NO 13
<211> LENGTH: 162
<212> TYPE: PRT
<213> ORGANISM: MSRV
<220> FEATURE:
```

```
<221> NAME/KEY: misc_feature
<222> LOCATION: (26)..(26)
<223> OTHER INFORMATION: Xaa = any amino acid
<220> FEATURE:
<221> NAME/KEY: misc_feature
<222> LOCATION: (42)..(42)
<223> OTHER INFORMATION: Xaa = any amino acid
<220> FEATURE:
<221> NAME/KEY: misc_feature
<222> LOCATION: (46)..(46)
<223> OTHER INFORMATION: Xaa = any amino acid

<400> SEQUENCE: 13

Gln Asn Arg Arg Ala Leu Asp Leu Leu Thr Ala Lys Arg Gly Gly Thr
1               5                   10                  15

Cys Leu Phe Leu Gly Glu Glu Cys Cys Xaa Tyr Val Asn Gln Ser Gly
            20                  25                  30

Ile Ile Thr Glu Lys Val Lys Glu Ile Xaa Asp Arg Ile Xaa Cys Arg
        35                  40                  45

Ala Glu Asp Leu Gln Asn Thr Ala Pro Trp Gly Leu Leu Ser Gln Trp
    50                  55                  60

Met Pro Trp Thr Leu Pro Phe Leu Gly Pro Leu Ala Ala Ile Ile Phe
65                  70                  75                  80

Leu Leu Leu Phe Gly Pro Cys Ile Phe Asn Phe Leu Val Lys Phe Val
                85                  90                  95

Ser Ser Arg Ile Glu Ala Val Lys Leu Gln Ile Val Leu Gln Met Glu
            100                 105                 110

Pro Gln Met Gln Ser Met Thr Lys Ile Tyr Arg Gly Pro Leu Asp Arg
        115                 120                 125

Pro Ala Arg Leu Cys Ser Asp Val Asn Asp Ile Glu Val Thr Pro Pro
    130                 135                 140

Glu Glu Ile Ser Thr Ala Gln Pro Leu Leu His Ser Asn Ser Val Gly
145                 150                 155                 160

Ser Ser

<210> SEQ ID NO 14
<211> LENGTH: 21
<212> TYPE: DNA
<213> ORGANISM: MSRV

<400> SEQUENCE: 14
ggcattgata gcacccatca g                                           21

<210> SEQ ID NO 15
<211> LENGTH: 21
<212> TYPE: DNA
<213> ORGANISM: MSRV

<400> SEQUENCE: 15
catgtcacca gggtggaata g                                           21

<210> SEQ ID NO 16
<211> LENGTH: 758
<212> TYPE: DNA
<213> ORGANISM: MSRV

<400> SEQUENCE: 16
ggcattgata gcacccatca gatggccaaa tcattattta ctggaccagg ccttttcaaa    60
actatcaagc agatagggcc cgtgaagcat gccaaagaaa taatcccctg ccttatcgcc   120
atgttccttc aggagaacaa agaacaggcc attcccagg ggaagactgg caactagatt    180
```

-continued

```
ttacccacat ggccaaatgt cagggatttc agcatctact agtctgggca gatactttca    240
ctggttgggt ggagtcttct ccttgtagga cagaaaagac ccaagaggta ataaaggcac    300
taatgaaata attcccagat ttggacttcc cccaggatta cagggtgaca atggccccgc    360
tttcaaggct gcagtaaccc agggagtatc ccaggtgtta ggcatacaat atcacttaca    420
ctgtgcctgg aggccacaat cctccagaaa agtcaagaaa atgaatgaaa cactcaaaga    480
tctaaaaaag ctaacccaag aaacccacat tgcatgacct gttctgttgc ctataacctt    540
actaagaatc cataactatc ccccaaaaag caggacttag cccatacgag atgctatatg    600
gatggccttt cctaaccaat gaccttgtgc ttgactgaga aatggccaac ttagttgcag    660
acatcacctc cttagccaaa tatcaacaag ttcttaaaac atcacaggga acctgtcccc    720
gagaggaggg aaaggaacta ttccaccctg gtgacatg                             758

<210> SEQ ID NO 17
<211> LENGTH: 25
<212> TYPE: DNA
<213> ORGANISM: MSRV

<400> SEQUENCE: 17
cggacatcca aagtgatggg aaacg                                            25

<210> SEQ ID NO 18
<211> LENGTH: 26
<212> TYPE: DNA
<213> ORGANISM: MSRV

<400> SEQUENCE: 18
ggacaggaaa gtaagactga gaaggc                                           26

<210> SEQ ID NO 19
<211> LENGTH: 26
<212> TYPE: DNA
<213> ORGANISM: MSRV

<400> SEQUENCE: 19
cctagaacgt attctggaga attggg                                           26

<210> SEQ ID NO 20
<211> LENGTH: 26
<212> TYPE: DNA
<213> ORGANISM: MSRV

<400> SEQUENCE: 20
tggctctcaa tggtcaaaca tacccg                                           26

<210> SEQ ID NO 21
<211> LENGTH: 1511
<212> TYPE: DNA
<213> ORGANISM: MSRV

<400> SEQUENCE: 21
cctagaacgt attctggaga attgggacca atgtgacact cagacgctaa gaaagaaacg     60
atttatattc ttctgcagta ccgcctggcc acaatatcct cttcaaggga gagaaacctg    120
gcttcctgag ggaagtataa attataacat catcttacag ctagacctct tctgtagaaa    180
ggagggcaaa tggagtgaag tgccatatgt gcaaactttc ttttcattaa gagacaactc    240
acaattatgt aaaaagtgtg gtttatgccc tacaggaagc cctcagagtc cacctcccta    300
```

-continued

```
ccccagcgtc ccctccccga ctccttcctc aactaataag gaccccccttt taacccaaac    360 ggtccaaaag gagatagaca aaggggtaaa caatgaacca aagagtgcca atattccccg     420
attatgcccc ctccaagcag tgagaggagg agaattcggc ccagccagag tgcctgtacc     480
tttttctctc tcagacttaa agcaaattaa aatagaccta ggtaaattct cagataaccc     540
tgacggctat attgatgttt tacaagggtt aggacaatcc tttgatctga catggagaga     600
tataatgtta ctactaaatc agacactaac cccaaatgag agaagtgccg ctgtaactgc     660
agcccgagag tttggcgatc tttggtatct cagtcaggcc aacaatagga tgacaacaga     720
ggaaagaaca actcccacag gccagcaggc agttcccagt gtagaccctc attgggacac     780
agaatcagaa catggagatt ggtgccacaa acatttgcta acttgcgtgc tagaaggact     840
gaggaaaact aggaagaagc ctatgaatta ctcaatgatg tccactataa cacagggaaa     900
ggaagaaaat cttactgctt ttctggacag actaagggag gcattgagga agcatacctc     960
cctgtcacct gactctattg aaggccaact aatcttaaag gataagttta tcactcagtc    1020
agctgcagac attagaaaaa acttcaaaag tctgccttag gcccggagca gaacttagaa    1080
accctattta acttggcatc ctcagttttt tataatagag atcaggagga gcaggcgaaa    1140
cgggacaaac gggataaaaa aaaaaggggg ggtccactac tttagtcatg gccctcaggc    1200
aagcagactt tggaggctct gcaaaaggga aaagctgggc aaatcaaatg cctaataggg    1260
ctggcttcca gtgcggtcta caaggacact ttaaaaaaga ttatccaagt agaaataagc    1320 cgccccccttg tccatgcccc ttacgtcaag ggaatcactg gaaggcccac tgccccaggg   1380
gatgaagata ctctgagtca gaagccatta accagatgat ccagcagcag gactgagggt    1440
gcccggggcg agcgccagcc catgccatca ccctcacaga gccccgggta tgtttgacca    1500
ttgagagcca a                                                         1511
```

```

<210> SEQ ID NO 22
<211> LENGTH: 352
<212> TYPE: PRT
<213> ORGANISM: MSRV

<400> SEQUENCE: 22

Leu Glu Arg Ile Leu Glu Asn Trp Asp Gln Cys Asp Thr Gln Thr Leu
1               5                   10                  15

Arg Lys Lys Arg Phe Ile Phe Phe Cys Ser Thr Ala Trp Pro Gln Tyr
            20                  25                  30

Pro Leu Gln Gly Arg Glu Thr Trp Leu Pro Glu Gly Ser Ile Asn Tyr
        35                  40                  45

Asn Ile Ile Leu Gln Leu Asp Leu Phe Cys Arg Lys Glu Gly Lys Trp
    50                  55                  60

Ser Glu Val Pro Tyr Val Gln Thr Phe Phe Ser Leu Arg Asp Asn Ser
65                  70                  75                  80

Gln Leu Cys Lys Lys Cys Gly Leu Cys Pro Thr Gly Ser Pro Gln Ser
                85                  90                  95

Pro Pro Pro Tyr Pro Ser Val Pro Ser Pro Thr Pro Ser Ser Thr Asn
            100                 105                 110

Lys Asp Pro Pro Leu Thr Gln Thr Val Gln Lys Glu Ile Asp Lys Gly
        115                 120                 125

Val Asn Asn Glu Pro Lys Ser Ala Asn Ile Pro Arg Leu Cys Pro Leu
    130                 135                 140

Gln Ala Val Arg Gly Gly Glu Phe Gly Pro Ala Arg Val Pro Val Pro
145                 150                 155                 160
```

-continued

```
Phe Ser Leu Ser Asp Leu Lys Gln Ile Lys Ile Asp Leu Gly Lys Phe
165 170 175

Ser Asp Asn Pro Asp Gly Tyr Ile Asp Val Leu Gln Gly Leu Gly Gln
180 185 190

Ser Phe Asp Leu Thr Trp Arg Asp Ile Met Leu Leu Leu Asn Gln Thr
195 200 205

Leu Thr Pro Asn Glu Arg Ser Ala Ala Val Thr Ala Ala Arg Glu Phe
210 215 220

Gly Asp Leu Trp Tyr Leu Ser Gln Ala Asn Asn Arg Met Thr Thr Glu
225 230 235 240

Glu Arg Thr Thr Pro Thr Gly Gln Gln Ala Val Pro Ser Val Asp Pro
245 250 255

His Trp Asp Thr Glu Ser Glu His Gly Asp Trp Cys His Lys His Leu
260 265 270

Leu Thr Cys Val Leu Glu Gly Leu Arg Lys Thr Arg Lys Lys Pro Met
275 280 285

Asn Tyr Ser Met Met Ser Thr Ile Thr Gln Gly Lys Glu Glu Asn Leu
290 295 300

Thr Ala Phe Leu Asp Arg Leu Arg Glu Ala Leu Arg Lys His Thr Ser
305 310 315 320

Leu Ser Pro Asp Ser Ile Glu Gly Gln Leu Ile Leu Lys Asp Lys Phe
325 330 335

Ile Thr Gln Ser Ala Ala Asp Ile Arg Lys Asn Phe Lys Ser Leu Pro
340 345 350

<210> SEQ ID NO 23
<211> LENGTH: 30
<212> TYPE: DNA
<213> ORGANISM: MSRV

<400> SEQUENCE: 23
tgctggaatt cgggatccta gaacgtattc 30

<210> SEQ ID NO 24
<211> LENGTH: 30
<212> TYPE: DNA
<213> ORGANISM: MSRV

<400> SEQUENCE: 24
agttctgctc cgaagcttag gcagactttt 30

<210> SEQ ID NO 25
<211> LENGTH: 398
<212> TYPE: PRT
<213> ORGANISM: MSRV

<400> SEQUENCE: 25

Met Gly Ser Ser His His His His His His Ser Ser Gly Leu Val Pro
1 5 10 15

Arg Gly Ser His Met Ala Ser Met Thr Gly Gly Gln Gln Met Gly Arg
20 25 30

Ile Leu Glu Arg Ile Leu Glu Asn Trp Asp Gln Cys Asp Thr Gln Thr
35 40 45

Leu Arg Lys Lys Arg Phe Ile Phe Phe Cys Ser Thr Ala Trp Pro Gln
50 55 60

Tyr Pro Leu Gln Gly Arg Glu Thr Trp Leu Pro Glu Gly Ser Ile Asn
65 70 75 80

Tyr Asn Ile Ile Leu Gln Leu Asp Leu Phe Cys Arg Lys Glu Gly Lys
                85                  90                  95

Trp Ser Glu Val Pro Tyr Val Gln Thr Phe Phe Ser Leu Arg Asp Asn
            100                 105                 110

Ser Gln Leu Cys Lys Lys Cys Gly Leu Cys Pro Thr Gly Ser Pro Gln
            115                 120                 125

Ser Pro Pro Pro Tyr Pro Ser Val Pro Ser Pro Thr Pro Ser Ser Thr
            130                 135                 140

Asn Lys Asp Pro Pro Leu Thr Gln Thr Val Gln Lys Glu Ile Asp Lys
145                 150                 155                 160

Gly Val Asn Asn Glu Pro Lys Ser Ala Asn Ile Pro Arg Leu Cys Pro
                165                 170                 175

Leu Gln Ala Val Arg Gly Gly Glu Phe Gly Pro Ala Arg Val Pro Val
            180                 185                 190

Pro Phe Ser Leu Ser Asp Leu Lys Gln Ile Lys Ile Asp Leu Gly Lys
            195                 200                 205

Phe Ser Asp Asn Pro Asp Gly Tyr Ile Asp Val Leu Gln Gly Leu Gly
            210                 215                 220

Gln Ser Phe Asp Leu Thr Trp Arg Asp Ile Met Leu Leu Leu Asn Gln
225                 230                 235                 240

Thr Leu Thr Pro Asn Glu Arg Ser Ala Ala Val Thr Ala Ala Arg Glu
                245                 250                 255

Phe Gly Asp Leu Trp Tyr Leu Ser Gln Ala Asn Asn Arg Met Thr Thr
            260                 265                 270

Glu Glu Arg Thr Thr Pro Thr Gly Gln Gln Ala Val Pro Ser Val Asp
            275                 280                 285

Pro His Trp Asp Thr Glu Ser Glu His Gly Asp Trp Cys His Lys His
            290                 295                 300

Leu Leu Thr Cys Val Leu Glu Gly Leu Arg Lys Thr Arg Lys Lys Pro
305                 310                 315                 320

Met Asn Tyr Ser Met Met Ser Thr Ile Thr Gln Gly Lys Glu Glu Asn
                325                 330                 335

Leu Thr Ala Phe Leu Asp Arg Leu Arg Glu Ala Leu Arg Lys His Thr
            340                 345                 350

Ser Leu Ser Pro Asp Ser Ile Glu Gly Gln Leu Ile Leu Lys Asp Lys
            355                 360                 365

Phe Ile Thr Gln Ser Ala Ala Asp Ile Arg Lys Asn Phe Lys Ser Leu
            370                 375                 380

Pro Lys Leu Ala Ala Ala Leu Glu His His His His His His
385                 390                 395

<210> SEQ ID NO 26
<211> LENGTH: 378
<212> TYPE: PRT
<213> ORGANISM: MSRV

<400> SEQUENCE: 26

Met Ala Ser Met Thr Gly Gly Gln Gln Met Gly Arg Ile Leu Glu Arg
1               5                   10                  15

Ile Leu Glu Asn Trp Asp Gln Cys Asp Thr Gln Thr Leu Arg Lys Lys
                20                  25                  30

Arg Phe Ile Phe Phe Cys Ser Thr Ala Trp Pro Gln Tyr Pro Leu Gln
            35                  40                  45

Gly Arg Glu Thr Trp Leu Pro Glu Gly Ser Ile Asn Tyr Asn Ile Ile

```
                50                  55                  60
Leu Gln Leu Asp Leu Phe Cys Arg Lys Glu Gly Lys Trp Ser Glu Val
 65                  70                  75                  80

Pro Tyr Val Gln Thr Phe Phe Ser Leu Arg Asp Asn Ser Gln Leu Cys
                 85                  90                  95

Lys Lys Cys Gly Leu Cys Pro Thr Gly Ser Pro Gln Ser Pro Pro Pro
                100                 105                 110

Tyr Pro Ser Val Pro Ser Pro Thr Pro Ser Ser Thr Asn Lys Asp Pro
                115                 120                 125

Pro Leu Thr Gln Thr Val Gln Lys Glu Ile Asp Lys Gly Val Asn Asn
130                 135                 140

Glu Pro Lys Ser Ala Asn Ile Pro Arg Leu Cys Pro Leu Gln Ala Val
145                 150                 155                 160

Arg Gly Gly Glu Phe Gly Pro Ala Arg Val Pro Val Pro Phe Ser Leu
                165                 170                 175

Ser Asp Leu Lys Gln Ile Lys Ile Asp Leu Gly Lys Phe Ser Asp Asn
                180                 185                 190

Pro Asp Gly Tyr Ile Asp Val Leu Gln Gly Leu Gly Gln Ser Phe Asp
                195                 200                 205

Leu Thr Trp Arg Asp Ile Met Leu Leu Leu Asn Gln Thr Leu Thr Pro
                210                 215                 220

Asn Glu Arg Ser Ala Ala Val Thr Ala Ala Arg Glu Phe Gly Asp Leu
225                 230                 235                 240

Trp Tyr Leu Ser Gln Ala Asn Asn Arg Met Thr Thr Glu Glu Arg Thr
                245                 250                 255

Thr Pro Thr Gly Gln Gln Ala Val Pro Ser Val Asp Pro His Trp Asp
                260                 265                 270

Thr Glu Ser Glu His Gly Asp Trp Cys His Lys His Leu Leu Thr Cys
                275                 280                 285

Val Leu Glu Gly Leu Arg Lys Thr Arg Lys Lys Pro Met Asn Tyr Ser
                290                 295                 300

Met Met Ser Thr Ile Thr Gln Gly Lys Glu Glu Asn Leu Thr Ala Phe
305                 310                 315                 320

Leu Asp Arg Leu Arg Glu Ala Leu Arg Lys His Thr Ser Leu Ser Pro
                325                 330                 335

Asp Ser Ile Glu Gly Gln Leu Ile Leu Lys Asp Lys Phe Ile Thr Gln
                340                 345                 350

Ser Ala Ala Asp Ile Arg Lys Asn Phe Lys Ser Leu Pro Lys Leu Ala
                355                 360                 365

Ala Ala Leu Glu His His His His His His
    370                 375

<210> SEQ ID NO 27
<211> LENGTH: 25
<212> TYPE: DNA
<213> ORGANISM: MSRV

<400> SEQUENCE: 27
cttggagggt gcataaccag ggaat                                        25

<210> SEQ ID NO 28
<211> LENGTH: 20
<212> TYPE: DNA
<213> ORGANISM: MSRV

<400> SEQUENCE: 28
```
tgtccgctgt gctcctgatc 20

<210> SEQ ID NO 29
<211> LENGTH: 25
<212> TYPE: DNA
<213> ORGANISM: MSRV

<400> SEQUENCE: 29
ctatgtcctt ttggactgtt tgggt 25

<210> SEQ ID NO 30
<211> LENGTH: 764
<212> TYPE: DNA
<213> ORGANISM: MSRV

<400> SEQUENCE: 30
tgtccgctgt gctcctgatc cagcacaggc gcccattgcc tctcccaatt gggctaaagg 60
cttgccattg ttcctgcaca gctaagtgcc tgggttcatc ctaatcgagc tgaacactag 120
tcactgggtt ccacggttct cttccatgac ccatggcttc taatagagct ataacactca 180
ctgcatggtc caagattcca ttccttggaa tccgtgagac caagaacccc aggtcagaga 240
acacaaggct tgccaccatg ttggaagcag cccaccacca ttttggaagc agcccgccac 300
tatcttggga gctctgggag caaggacccc aggtaacaat ttggtgacca cgaagggacc 360
tgaatccgca accatgaagg gatctccaaa gcaattggaa atgttcctcc caaggcaaaa 420
atgcccctaa gatgtattct ggagaattgg gaccaatttg accctcagac agtaagaaaa 480
aaatgactta tattcttctg cagtaccgcc ctggccacga tatcctcttc aaggggggaga 540 aacctggcct cctgagggaa gtataaatta taacaccatc ttacagctag acctgttttg 600
tagaaaagga ggcaaatgga gtgaagtgcc atatttacaa actttctttt cattaaaaga 660
caactcgcaa ttatgttaac agtgtgattt gtgttcctac acggaagccc tcagattcta 720
ctccccaccc ccggcatctc ccctgaatcc ctccccaact tatt 764

<210> SEQ ID NO 31
<211> LENGTH: 800
<212> TYPE: DNA
<213> ORGANISM: MSRV

<400> SEQUENCE: 31
tgtccgctgt gctcctgatc cagcacaggc gcccattgcc tctcccaatt gggctaaagg 60
cttgccattg ttcctgcaca gctaagtgcc tgggttcatc ctaatcgagc tgaacactag 120
tcactgggtt ccacggttct cttccatgac ccatggcttc taatagagct ataacactca 180
ctgcatggtc caagattcca ttccttggaa tccgtgagac caagaacccc aggtcagaga 240
acacaaggct tgccaccatg ttggaagcag cccaccacca ttttggaagc ggcccgccac 300
tatcttggga gctctgggag caaggacccc caggtaacaa tttggtgacc acgaagggac 360
ctgaatccgc aaccatgaag ggatctccaa agcaattgga aatgttcctc ccaaggcaaa 420
aatgccccta agatgtattc tggagaattg ggaccaatct gaccctcaga cagtaagaaa 480
aaaaatgact tatattcttc tgcagtaccg cctggccacg gatatcctct tcaaggggga 540
gaaacctggc ctcctgaggg aagtataaat tataacacca tcttacagct agacctgttt 600
tgtagaaaag gaggcaaatg gagtgaagtg ccatatttac aaactttctt ttcattaaaa 660
gacaactcgc aattatgtaa acagtgtgat ttgtgtccta caggaagccc tcagatctac 720

```
ctccctaccc cggcatctcc ctgactcctt ccccaactaa taaggaccca cttcagccca    780
aacagtccaa aaggacatag                                                800
```

<210> SEQ ID NO 32
<211> LENGTH: 65
<212> TYPE: PRT
<213> ORGANISM: MSRV

<400> SEQUENCE: 32

```
Pro Met Ala Ser Asn Arg Ala Ile Thr Leu Thr Ala Trp Ser Lys Ile
1               5                   10                  15

Pro Phe Leu Gly Ile Arg Glu Thr Lys Asn Pro Arg Ser Glu Asn Thr
            20                  25                  30

Arg Leu Ala Thr Met Leu Glu Ala Ala His His His Phe Gly Ser Ser
        35                  40                  45

Pro Pro Leu Ser Trp Glu Leu Trp Glu Gln Gly Pro Gln Val Thr Ile
    50                  55                  60

Trp
65
```

<210> SEQ ID NO 33
<211> LENGTH: 26
<212> TYPE: DNA
<213> ORGANISM: MSRV

<400> SEQUENCE: 33

```
tcatgcaact gcactcttct ggtccg                                          26
```

<210> SEQ ID NO 34
<211> LENGTH: 28
<212> TYPE: DNA
<213> ORGANISM: MSRV

<400> SEQUENCE: 34

```
tcttgcacta acctccactg tccgttgg                                        28
```

<210> SEQ ID NO 35
<211> LENGTH: 28
<212> TYPE: DNA
<213> ORGANISM: MSRV

<400> SEQUENCE: 35

```
atcccccagt aacaatttgg tgaccacg                                        28
```

<210> SEQ ID NO 36
<211> LENGTH: 31
<212> TYPE: DNA
<213> ORGANISM: MSRV

<400> SEQUENCE: 36

```
tcgggtctaa gagggtactt cctttggtag g                                    31
```

<210> SEQ ID NO 37
<211> LENGTH: 25
<212> TYPE: DNA
<213> ORGANISM: MSRV

<400> SEQUENCE: 37

```
ttacgcaggt ctcagggatg agctt                                           25
```

<210> SEQ ID NO 38

-continued

```
<211> LENGTH: 33
<212> TYPE: DNA
<213> ORGANISM: MSRV

<400> SEQUENCE: 38
cggcagtagc agtcttagta tctgaagcag tta 33

<210> SEQ ID NO 39
<211> LENGTH: 28
<212> TYPE: DNA
<213> ORGANISM: MSRV

<400> SEQUENCE: 39
ggtacggagg gtttcatgta gttttgag 28

<210> SEQ ID NO 40
<211> LENGTH: 1247
<212> TYPE: DNA
<213> ORGANISM: MSRV
<220> FEATURE:
<221> NAME/KEY: misc_feature
<222> LOCATION: (1240)..(1240)
<223> OTHER INFORMATION: n = a, g, c or t/u
<220> FEATURE:
<221> NAME/KEY: misc_feature
<222> LOCATION: (1246)..(1246)
<223> OTHER INFORMATION: n = a, g, c or t/u
<400> SEQUENCE: 40
atgggcagca gccatcatca tcatcatcac agcagcggcc tggtgccgcg cggcagccat 60
atggctagca tgactggtgg acagcaaatg ggtcggatcc tagaacgtat tctggagaat 120
tgggaccaat gtgacactca gacgctaaga aagaaacgat ttatattctt ctgcagtacc 180
gcctggccac aatatcctct tcaagggaga gaaacctggc ttcctgaggg aagtataaat 240
tataacatca tcttacagct agacctcttc tgtagaaagg agggcaaatg gagtgaagtg 300
ccatatgtgc aaactttctt ttcattaaga gacaactcac aattatgtaa aaagtgtggt 360
ttatgcccta caggaagccc tcagagtcca cctccctacc ccagcgtccc ctccccgact 420
ccttcctcaa ctaataagga cccccccttta acccaaacgg tccaaaagga gatagacaaa 480
ggggtaaaca atgaaccaaa gagtgccaat attccccgat tatgcccccct ccaagcagtg 540
agaggaggag aattcggccc agccagagtg cctgtacctt tttctctctc agacttaaag 600
caaattaaaa tagacctagg taaattctca gataaccctg acggctatat tgatgtttta 660
caagggttag gacaatcctt tgatctgaca tggagagata taatgttact actaaatcag 720
acactaaccc caaatgagag aagtgccgct gtaactgcag cccgagagtt tggcgatctt 780
tggtatctca gtcaggccaa caataggatg acaacagagg aaagaacaac tcccacaggc 840
cagcaggcag ttcccagtgt agaccctcat tgggacacag aatcagaaca tggagattgg 900
tgccacaaac atttgctaac ttgcgtgcta gaaggactga ggaaaactag gaagaagcct 960
atgaattact caatgatgtc cactataaca cagggaaagg aagaaaatct tactgctttt 1020
ctggacagac taagggaggc attgaggaag catacctccc tgtcacctga ctctattgaa 1080
ggccaactaa tcttaaagga taagtttatc actcagtcag ctgcagacat tagaaaaaac 1140
ttcaaaagtc tgcctaagct tgcggccgca ctcgagcacc accaccacca ccactgagat 1200
ccggctgcta acaaagcccg aaaggaagct gagttgggtn gtggcna 1247

<210> SEQ ID NO 41
<211> LENGTH: 1186
```

-continued

<212> TYPE: DNA
<213> ORGANISM: MSRV

<400> SEQUENCE: 41

```
atggctagca tgactggtgg acagcaaatg ggtcggatcc tagaacgtat tctggagaat     60
tgggaccaat gtgacactca gacgctaaga aagaaacgat ttatattctt ctgcagtacc    120
gcctggccac aatatcctct tcaagggaga gaaacctggc ttcctgaggg aagtataaat    180
tataacatca tcttacagct agacctcttc tgtagaaagg agggcaaatg gagtgaagtg    240
ccatatgtgc aaactttctt ttcattaaga gacaactcac aattatgtaa aaagtgtggt    300
ttatgcccta caggaagccc tcagagtcca cctccctacc ccagcgtccc ctccccgact    360
ccttcctcaa ctaataagga ccccccttta acccaaacgg tccaaaagga gatagacaaa    420
ggggtaaaca atgaaccaaa gagtgccaat attccccgat tatgccccct ccaagcagtg    480
agaggaggag aattcggccc agccagagtg cctgtacctt tttctctctc agacttaaag    540
caaattaaaa tagacctagg taaattctca gataaccctg acggctatat tgatgtttta    600
caagggttag gacaatcctt tgatctgaca tggagagata taatgttact actaaatcag    660
acactaaccc caaatgagag aagtgccgct gtaactgcag cccgagagtt tggcgatctt    720
tggtatctca gtcaggccaa caataggatg acaacagagg aaagaacaac tcccacaggc    780
cagcaggcag ttcccagtgt agaccctcat tgggacacag aatcagaaca tggagattgg    840
tgccacaaac atttgctaac ttgcgtgcta gaaggactga ggaaaactag gaagaagcct    900
atgaattact caatgatgtc cactataaca cagggaaagg aagaaaatct tactgctttt    960
ctggacagac taagggaggc attgaggaag catacctccc tgtcacctga ctctattgaa   1020
ggccaactaa tcttaaagga taagtttatc actcagtcag ctgcagacat tagaaaaaac   1080
ttcaaaagtc tgcctaagct tgcggccgca ctcgagcacc accaccacca ccactgagat   1140
ccggctgcta acaaagcccg aaaggaagct gagttggctg gtggca                  1186
```

<210> SEQ ID NO 42
<211> LENGTH: 2030
<212> TYPE: DNA
<213> ORGANISM: MSRV

<400> SEQUENCE: 42

```
atggccctcc cttatcatac ttttctcttt actgttctct tacccccttt cgctctcact     60
gcacccccctc catgctgctg tacaaccagt agctcccctt accaagagtt tctatgaaga    120
acgcggcttc ctggaaatat tgatgcccca tcatatagga gtttatctaa gggaaactcc    180
accttcactg cccacaccca tatgccccgc aactgctata actctgccac tctttgcatg    240
catgcaaata ctcattattg gacagggaaa atgattaatc ctagttgtcc tggaggactt    300
ggagccactg tctgttggac ttacttcacc cataccagta tgtctgatgg gggtggaatt    360
caaggtcagg caagagaaaa acaagtaaag gaagcaatct cccaactgac ccggggacat    420
agcaccccta gcccctacaa aggactagtt ctctcaaaac tacatgaaac cctccgtacc    480
catactcgcc tggtgagcct atttaatacc accctcactc ggctccatga ggtctcagcc    540
caaaacccta ctaactgttg gatgtgcctc cccctgcact tcaggccata catttcaatc    600
cctgttcctg aacaatggaa caacttcagc acagaaataa acaccacttc cgttttagta    660
ggacctcttg tttccaatct ggaaataacc catacctcaa acctcacctg tgtaaaattt    720
agcaatacta tagacacaac cagctcccaa tgcatcaggt gggtaacacc tcccacacga    780
```

```
atagtctgcc taccctcagg aatatttttt gtctgtggta cctcagccta tcattgtttg      840
aatggctctt cagaatctat gtgcttcctc tcattcttag tgcccccta t gaccatctac     900 actgaacaag atttatacaa tcatgtcgta cctaagcccc acaacaaaag agtacccatt      960
cttccttttg ttatcagagc aggagtgcta ggcagactag gtactggcat tggcagtatc     1020
acaacctcta ctcagttcta ctacaaacta tctcaagaaa taaatggtga catggaacag     1080
gtcactgact ccctggtcac cttgcaagat caacttaact ccctagcagc agtagtcctt     1140
caaaatcgaa gagctttaga cttgctaacc gccaaaagag ggggaacctg tttattttta     1200
ggagaagaac gctgttatta tgttaatcaa tccagaattg tcactgagaa agttaaagaa     1260
attcgagatc gaatacaatg tagagcagag gagcttcaaa acaccgaacg ctggggcctc     1320
ctcagccaat ggatgccctg ggttctcccc ttcttaggac tctagcagc tctaatattg      1380 ttactcctct ttggaccctg tatctttaac ctccttgtta gtttgtctc ttccagaatt      1440 gaagctgtaa agctacagat ggtcttacaa atggaacccc agatggagtc catgactaag     1500
atccaccgtg accctggga ccggcctgct agcccatgct ccgatgttaa tgacattgaa      1560 ggcaccctc ccgaggaaat ctcaactgca caacccctac tatgccccaa ttcagcggga     1620
agcagttaga gcggtcatca gccaacctcc ccaacagcac ttgggttttc ctgttgagag     1680
gggggactga gagacaggac tagctggatt tcctaggcca acgaagaatc cctaagccta     1740
gctgggaagg tgactgcatc cacctctaaa catggggctt gcaacttagc tcacacccga     1800
ccaatcagag agctcactaa aatgctaatt aggcaaaaat aggaggtaaa gaaatagcca     1860
atcatctatt gcctgagagc acagcgggag ggacaaggat cgggatataa acccaggcat     1920
tcgagccggc aacggcaacc ccctttgggt cccctccctt tgtatgggcg ctctgttttc     1980
actctatttc actctattaa atcttgcaac tgaaaaaaaa aaaaaaaaa                 2030
```

<210> SEQ ID NO 43
<211> LENGTH: 2055
<212> TYPE: DNA
<213> ORGANISM: MSRV

<400> SEQUENCE: 43

```
cagcaaccc c ctttgggtcc cctcccattg tatgggagct ctgttttcac tctatttcac      60
tctattaaat catgcaactg cactcttctg gtccgtgttt tttatggctc aagctgagct     120
tttgttcgcc atccaccact gctgtttgcc accgtcacag acccgctgct gacttccatc     180
cctttggatc cagcagagtg tccgctgtgc tcctgatcca gcacaggcgc ccattgcctc     240
tcccaattgg gctaaaggct tgccattgtt cctgcacagc taagtgcctg ggttcatcct     300
aatcgagctg aacactagtc actgggttcc acggttctct tccatgaccc atggcttcta     360
atagagctat aacactcact gcatggtcca agattccatt ccttggaatc cgtgagacca     420 agaacccag gtcagagaac acaaggcttg ccaccatgtt ggaagcagcc caccaccatt     480
ttggaagcag cccgccacta tcttgggagc tctgggagca aggaccccag gtaacaattt     540
ggtgaccacg aagggacctg aatccgcaac catgaaggga tctccaaagc aatgggaaac     600 gttcccccg aggcaaaaat gcccctagaa cgtattctgg agaattggga ccaatgtgac      660
actcagacgt aagaaagaa acgatttata ttcttctgca gtaccgcctg ccacaatat       720 cctcttcaag ggagagaaac ctggcttcct gagggaagta taaattataa catcatctta     780
cagctagacc tcttctgtag aaaggagggc aaatggagtg aagtgccata tgtgcaaact     840
ttcttttcat taagagacaa ctcacaatta tgtaaaaagt gtggtttatg ccctacagga     900
```

-continued

| | |
|---|---|
| agccctcaga gtccacctcc ctaccccagc gtcccctccc cgactccttc ctcaactaat | 960 |
| aaggacccccc ctttaaccca aacggtccaa aaggagatag acaaggggt aaacaatgaa | 1020 |
| ccaaagagtg ccaatattcc ccgattatgc cccctccaag cagtgagagg aggagaattc | 1080 |
| ggcccagcca gagtgcctgt accttttttct ctctcagact taaagcaaat taaaatagac | 1140 |
| ctaggtaaat tctcagataa ccctgacggc tatattgatg ttttacaagg gttaggacaa | 1200 |
| tcctttgatc tgacatggag agatataatg ttactactaa atcagacact aaccccaaat | 1260 |
| gagagaagtg ccgctgtaac tgcagcccga gagtttggcg atctttggta tctcagtcag | 1320 |
| gccaacaata ggatgacaac agaggaaaga acaactccca caggccagca ggcagttccc | 1380 |
| agtgtagacc ctcattggga cacagaatca gaacatggag attggtgcca caaacatttg | 1440 |
| ctaacttgcg tgctagaagg actgaggaaa actaggaaga agcctatgaa ttactcaatg | 1500 |
| atgtccacta taacacaggg aaaggaagaa aatcttactg cttttctgga cagactaagg | 1560 |
| gaggcattga ggaagcatac ctccctgtca cctgactcta ttgaaggcca actaatctta | 1620 |
| aaggataagt ttatcactca gtcagctgca gacattagaa aaaaacttca aaagtccgtc | 1680 |
| ttaggctcgg aacaaaactt agaaacccta ttgaacttgg caacctcggt ttttttataat | 1740 |
| agagatcagg aggagcaggc agaatgggac aaatgggata aaaaaaaaag ggccaccgct | 1800 |
| ttagtcatgg ccctcaggca agcggacttt ggaggctctg gaaaagggaa aagctgggca | 1860 |
| aataggaagc ctaataggc ttgcttccag tgcggtctac aaggacactt taaaaaagat | 1920 |
| tgtccaaata gaaataagcc gcccccttgt ccatgcccct tacgtcaagg gaatcactgg | 1980 |
| aaggcccact gccccagggg atcaagatac tctgagtcag aagccattaa ccagatgatc | 2040 |
| cagcagcagg actga | 2055 |

<210> SEQ ID NO 44
<211> LENGTH: 1197
<212> TYPE: DNA
<213> ORGANISM: MSRV

<400> SEQUENCE: 44

| | |
|---|---|
| ggacccgtag tatggggtaa tcccctccgg gaaaccaagc cccagtactc agaagaagaa | 60 |
| atagaatggg gaacctcacg aggacatggt ttcctcccct caggatggct agccactgaa | 120 |
| gaaggaaaaa tacttttgct ggcagctaac caatggaaat tacttaaaac ccttcagcaa | 180 |
| accttccact taggcattga tagcacccat cagatagcca aatcattatt tactggacca | 240 |
| ggccttttca aaactatcaa gcagatagtc agggcctgtg aagtgtgcca agaaataat | 300 |
| cccctgcctt atcgccaagc tccttcagga gaacaaagaa caggcaatta cccaagagaa | 360 |
| gactggcaac tagattttat ccacatgcca aaatcacagg gatttcagtg tctactagtc | 420 |
| tgggtagata cttcactgg ttgggcagag gccttcccct gtaggacaga aaagttccaa | 480 |
| gaggtaataa aggcactagt tcatgaagta attcccagat tcggacttcc ctgaggctta | 540 |
| cagagtgaca atggtcctgc tttcaaggcc acagtaaccc agggagtatc ccaggcgtta | 600 |
| ggtatagaat atcacttaca ctgcacctag aggccacaat cctcagggaa ggttgagaaa | 660 |
| atgaaaacac tcaaacgaca tctaaacaag ctacccagg aaacccacct cgcatggtct | 720 |
| gctctgttgt ctatagcctt actaagaatc caaaactctc cccaaaaggc aggacttagc | 780 |
| ccatacagaa tgctgtatgg acggtccttc ctaaccaatg accttctgct tgaccaagag | 840 |
| atggccaact tagttgcaga catcacctcc ttagccaaat atcaacaagt tcttaaaaca | 900 |

-continued

```
ttacaaggag cctgtccccg agaggaggga aaagaaatat tccaccctgg tgtcatggta    960
ttagtcaagt cccttccctc taattcccca tccctagaca catcctgggg aggaccctac   1020
ccagtcattt tatctatccc aactgcggtt aaagtggctg gagtggagtc ttggatacat   1080
cacactcgaa tcaaaccctg gatactgccg aaggaacccg aaaatccagg ggacaacgct   1140
agctatttct ttgaacctct agaggatctg tgcctgctct tcaagcaaca accgtga      1197


<210> SEQ ID NO 45
<211> LENGTH: 1718
<212> TYPE: DNA
<213> ORGANISM: MSRV

<400> SEQUENCE: 45
gagaatagca gcataagttg gctggcagaa gtagggaaag acagcaagaa gtaaagaaaa     60
aaaggagaaa gtcagagaaa gaaaaaaaga gaggaagaaa caaagaagaa cttgaagaga    120
gaaagaagta gtaaagaaaa aacagtatac cctattcctt taaaagccag ggtaaatttc    180
tgtctaccta gccaaggcat attcttctta tgtggaacat caacctatat ctgcctcccc    240
actaactgga caggcaccag aaccttagtc tttctaagtc ccaacattaa cattgcccca    300
ggaaatcaga ccctattggt acctgtcaaa gctaaagtcc gtcagtgcag agccatacaa    360
ctaatatccc tatttatagg gttaggaatg gctactgcta caggaactgg aatagccggt    420
ttatctactt cattatccta ctaccataca ctctcaaaga atttctcaga cagtttgcaa    480
gaaataatga aatctattct tactttacaa tcccaattag actctttggc agcaatgact    540
ctccaaaacc gccgaggccc acacctcctc actgctgaga aaggaggact ctgcaccttc    600
ttaggggaag agtgttgttt ttacactaac cagtcaggga tagtacgaga tgccacctgg    660
catttacagg aaagggcttc tgatatcaga caatgccttt caaactctta taccaacctc    720
tggagttggg caacatggct tcttccattt ctaggtccca tggcagccat cttgctgtta    780
ctcacctttg ggccctgtat ttttaagctt cttgtcaaat ttgtttcctc taggatcgaa    840
gccatcaagc tacagatggt cttacaaatg gaaccccaaa tgagttcaac taacaacttc    900
taccaaggac ccctggaacg atccactggc acttccacta gcctagagat tcccctctgg    960
aagacactac aactgcaggg ccccttcttt gcccctatcc agcaggaagt agctagagcg   1020
gtcatcggcc aaattcccaa cagcagttgg ggtgtcctgt ttagaggggg gattgaagag   1080
tgacagcctg ctggcagcct cacagccctc gttggatctc agtgcctcct cagccttggt   1140
gcccactctg gccgtgcttg aggagccctt cagcctgcca ctgcactgtg ggagcctctt   1200
tctgggctgg acaaggccgg agccagctcc ctcagcttgc agggaggtat ggagggagag   1260
atgcaggcgg gaaccagggc tgcgcatggc gcttgcgggc cagcatgagt tccaggtggg   1320
cgtgggctcg gcgggcccca cactcgggca gtgaggggct tagcacctgg gccagacaga   1380
tgctgtgctc aacttcttcg ctgggcctta gctgccttcc ccgtggggca gggctacggg   1440
aacatgcagc ctgcccatgc ttgagccccc caccccgccg tgggttcytg cacagcccaa   1500
gcttcccgga caagcaccac cccttatcca cggtgcccag tcccatcaac cacccaaggg   1560
ttgaggagtg cgggcacaca gcgcgggatt ggcaggcagt tccacttgcg gccttggtgc   1620
gggatccact gcgtgaagcc agctgggctc ctgagtctgg tggggacttg gagaatcttt   1680
atgtctagct aagggattgt aaatacacca atcagcac                           1718
```

The invention claimed is:

1. An isolated polynucleotide, comprising a nucleic acid having a nucleotide sequence selected from the group consisting of:
   (i) the full-length sequences set forth in SEQ ID NO: 6, SEQ ID NO: 9, and SEQ ID NO: 12; and
   (ii) the full-length complementary sequences to the sequences set forth in (i).

2. An isolated retroviral polynucleotide comprising an env gene, wherein said env gene comprises a nucleic acid having a nucleotide sequence selected from the group consisting of the full-length sequence set forth in SEQ ID NO: 9, and the full-length complementary sequence thereof.

3. An isolated retroviral polynucleotide comprising an env gene, wherein said env gene encodes a polypeptide having the peptide sequence set forth in SEQ ID NO: 10.

4. An isolated fragment comprising a polynucleotide having a nucleotide sequence selected from the group consisting of:
   (i) the full-length sequences set forth in SEQ ID NO: 6, SEQ ID NO: 9, and SEQ ID NO: 12; and
   (ii) the full-length complementary sequences to the sequences set forth in (i).

5. The fragment according to claim 4, consisting of a polynucleotide having a nucleotide sequence selected from the group consisting of:
   (i) the full-length sequences set forth in SEQ ID NO: 6, SEQ ID NO: 9, and SEQ ID NO: 12; and
   (ii) the full-length complementary sequences to the sequences set forth in (i).

6. A method for detecting a retrovirus associated with multiple sclerosis and/or rheumatoid arthritis, the method comprising:
   a) obtaining and preparing a biological sample from a patient suspected of being infected with a multiple sclerosis- or rheumatoid arthritis-related retrovirus,
   b) transferring nucleic acids present in the sample to a solid substrate and denaturing the nucleic acids,
   c) contacting the nucleic acids of the sample obtained in b) with a probe comprising the isolated fragment according to claim 4, under conditions that allow specific binding between the probe and target RNA and/or DNA,
   d) washing the sample of c) to remove nonspecifically bound nucleic acids, and
   e) detecting a hybridization complex that remains on the solid substrate.

7. The isolated polynucleotide according to claim 1, wherein said polynucleotide is DNA.

8. The isolated polynucleotide according to claim 1, wherein said polynucleotide is RNA.

9. The isolated polynucleotide according to claim 1, wherein said polynucleotide is genomic DNA.

10. A recombinant vector comprising the polynucleotide defined in claim 1.

11. An expression vector comprising the polynucleotide defined in claim 1.

12. The isolated polynucleotide of claim 1, wherein said nucleotide sequence is selected from the group consisting of:
    (a) the full-length sequences set forth in SEQ ID NO: 6 and SEQ ID NO: 9; and
    (b) the full-length complementary sequences to the sequences set forth in (a).

13. An isolated polynucleotide encoding an amino acid sequence as set forth in SEQ ID NO: 7, SEQ ID NO: 10, or SEQ ID NO: 13.

* * * * *